(12) United States Patent
Shi et al.

(10) Patent No.: US 12,109,289 B2
(45) Date of Patent: *Oct. 8, 2024

(54) COMPOSITIONS FOR IMPARTING COLOR AND TONE TO THE HAIR

(71) Applicant: L'Oreal, Paris (FR)

(72) Inventors: Minli Shi, Jersey City, NJ (US); Kimberly Dreher, Brielle, NJ (US); Leslie Warner, Jersey City, NJ (US); Brian Kluck, Piscataway, NJ (US)

(73) Assignee: L'OREAL, Paris (FR)

( * ) Notice: Subject to any disclaimer, the term of this patent is extended or adjusted under 35 U.S.C. 154(b) by 90 days.

This patent is subject to a terminal disclaimer.

(21) Appl. No.: 17/853,722

(22) Filed: Jun. 29, 2022

(65) Prior Publication Data

US 2023/0037788 A1 Feb. 9, 2023

Related U.S. Application Data

(60) Provisional application No. 63/217,225, filed on Jun. 30, 2021.

(30) Foreign Application Priority Data

Sep. 17, 2021 (FR) ...................................... 2109796

(51) Int. Cl.
| | | |
|---|---|---|
| *A61Q 5/10* | (2006.01) | |
| *A61K 8/362* | (2006.01) | |
| *A61K 8/41* | (2006.01) | |
| *A61K 8/44* | (2006.01) | |
| *A61K 8/46* | (2006.01) | |
| *A61K 8/92* | (2006.01) | |

(52) U.S. Cl.
CPC ................ *A61K 8/41* (2013.01); *A61K 8/362* (2013.01); *A61K 8/415* (2013.01); *A61K 8/44* (2013.01); *A61K 8/466* (2013.01); *A61K 8/92* (2013.01); *A61Q 5/10* (2013.01); *A61K 2800/43* (2013.01); *A61K 2800/596* (2013.01)

(58) Field of Classification Search
CPC .......... A61K 8/41; A61K 8/362; A61K 8/415; A61K 8/44; A61K 8/466; A61K 8/92; A61K 2800/43; A61K 2800/596; A61K 8/342; A61K 8/365; A61K 8/39; A61K 8/411; A61K 8/42; A61Q 5/10
USPC ............................................................ 8/405
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,288,770 A | 11/1966 | Butler | |
| 3,412,019 A | 11/1968 | Hoover et al. | |
| 3,472,840 A | 10/1969 | Stone et al. | |
| 3,589,978 A | 6/1971 | Kamal et al. | |
| 3,632,559 A | 1/1972 | Matter et al. | |
| 3,874,870 A | 4/1975 | Green et al. | |
| 3,917,817 A | 11/1975 | Vanlerberghe et al. | |
| 3,929,990 A | 12/1975 | Green et al. | |
| 3,966,904 A | 6/1976 | Green et al. | |
| 4,001,432 A | 1/1977 | Green et al. | |
| 4,003,699 A | 1/1977 | Rose et al. | |
| 4,005,193 A | 1/1977 | Green et al. | |
| 4,013,787 A | 3/1977 | Vanlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,133,957 A | 1/1979 | Riew | |
| 4,137,180 A | 1/1979 | Naik et al. | |

(Continued)

FOREIGN PATENT DOCUMENTS

| | | |
|---|---|---|
| CN | 106955248 A | 7/2017 |
| CN | 110193008 A | 9/2019 |

(Continued)

OTHER PUBLICATIONS

Porter, M.R., "Handbook of Surfactants," published by Blackie & Son (Glasgow and London), 1991, pp. 116-178.
Copending As-filed U.S. Appl. No. 17/101,206, filed Nov. 23, 2020.
Copending As-filed U.S. Appl. No. 17/133,376, filed Dec. 23, 2020.
Copending As-filed U.S. Appl. No. 17/132,697, filed Dec. 23, 2020.
Copending As-filed U.S. Appl. No. 16/915,365, filed Jun. 29, 2020.
International Search Report and Written Opinion for counterpart Application No. PCT/US2020/067153, dated Apr. 29, 2021.
Third-Party Submission Under 37 C.F.R. 1.290 for U.S. Appl. No. 17/133,376, dated Jan. 27, 2022 with exhibits.
International Search Report for counterpart Application No. PCT/US2020/067155, dated May 3, 2021.

(Continued)

*Primary Examiner* — Eisa B Elhilo
(74) *Attorney, Agent, or Firm* — THE MARBURY LAW GROUP, PLLC

(57) ABSTRACT

The present disclosure relates to compositions for altering the tone or color of the hair comprising at least one amino acid, at least one carboxylic acid, monoethanolamine, at least one oxidation base chosen from toluene-2,5-diamine, acid salts thereof, or solvates thereof, and a coupler system comprising one or more couplers chosen from 2,4-diaminophenoxyethanol, meta-aminophenol, derivatives thereof, addition salts thereof, solvates thereof, solvates of salts thereof, or mixtures thereof. The disclosure also relates to methods of using the compositions and kits comprising the compositions.

20 Claims, No Drawings

(56) References Cited

U.S. PATENT DOCUMENTS

| | | |
|---|---|---|
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,362,528 A | 12/1982 | Grollier et al. |
| 4,381,919 A | 5/1983 | Jacquet et al. |
| 4,422,853 A | 12/1983 | Jacquet et al. |
| 4,579,732 A | 4/1986 | Grollier et al. |
| 4,591,610 A | 5/1986 | Grollier |
| 4,608,250 A | 8/1986 | Jacquet et al. |
| 4,761,273 A | 8/1988 | Grollier et al. |
| 4,772,462 A | 9/1988 | Boothe et al. |
| 4,777,040 A | 10/1988 | Grollier et al. |
| 4,855,130 A | 8/1989 | Konrad et al. |
| 4,874,554 A | 10/1989 | Lange et al. |
| 4,948,579 A | 8/1990 | Jacquet et al. |
| 4,970,066 A | 11/1990 | Grollier et al. |
| 5,061,289 A | 10/1991 | Clausen et al. |
| 5,196,189 A | 3/1993 | Jacquet et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 5,951,969 A | 9/1999 | Golinski et al. |
| 5,985,803 A | 11/1999 | Rizvi et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,358,502 B1 | 3/2002 | Tanabe et al. |
| 6,645,258 B2 | 11/2003 | Vidal et al. |
| 6,730,789 B1 | 5/2004 | Birault et al. |
| 7,507,261 B2 | 3/2009 | Nobuto et al. |
| 8,236,063 B2 | 8/2012 | Reichert et al. |
| 8,241,370 B2 | 8/2012 | Legrand et al. |
| 9,095,518 B2 | 8/2015 | Pressly et al. |
| 9,114,088 B2 | 8/2015 | Konno et al. |
| 9,326,926 B2 | 5/2016 | Pressly et al. |
| 9,597,273 B2 | 3/2017 | Pressly et al. |
| 10,987,291 B2 | 4/2021 | Manneck et al. |
| 11,160,739 B1 | 11/2021 | Shi et al. |
| 11,337,906 B2 | 5/2022 | Lee et al. |
| 11,559,474 B2 | 1/2023 | Degeorge et al. |
| 11,857,660 B2 * | 1/2024 | Shi .................. A61K 8/44 |
| 2001/0052354 A1 | 12/2001 | Nishibe et al. |
| 2002/0050013 A1 | 5/2002 | Vidal et al. |
| 2003/0019051 A9 | 1/2003 | Vidal et al. |
| 2004/0235700 A1 | 11/2004 | Legrand et al. |
| 2006/0140887 A1 | 6/2006 | Molenda et al. |
| 2007/0107142 A1 | 5/2007 | Nguye et al. |
| 2008/0317687 A1 | 12/2008 | Howe et al. |
| 2010/0305064 A1 | 12/2010 | Walsh |
| 2011/0150804 A1 | 6/2011 | Nojiri et al. |
| 2012/0005843 A1 | 1/2012 | Benade et al. |
| 2012/0031423 A1 | 2/2012 | Wood et al. |
| 2012/0048288 A1 | 3/2012 | Reichert et al. |
| 2012/0114583 A1 | 5/2012 | Giesen et al. |
| 2012/0329650 A1 | 12/2012 | Lopez-Cervantes |
| 2013/0125914 A1 | 5/2013 | Battermann et al. |
| 2013/0149274 A1 | 6/2013 | Nguyen et al. |
| 2013/0156716 A1 | 6/2013 | Yontz |
| 2014/0158150 A1 | 6/2014 | Schoepgens et al. |
| 2014/0171354 A1 | 6/2014 | Miralles et al. |
| 2014/0246041 A1 | 9/2014 | Krueger |
| 2015/0004117 A1 | 1/2015 | Tan et al. |
| 2015/0004119 A1 | 1/2015 | Tan et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0202125 A1 | 7/2015 | Charrier et al. |
| 2015/0202142 A1 | 7/2015 | Charrier et al. |
| 2015/0283041 A1 | 10/2015 | Benn et al. |
| 2015/0290101 A1 | 10/2015 | Pressly et al. |
| 2015/0305469 A1 | 10/2015 | Paul |
| 2015/0328102 A1 | 11/2015 | Pressly et al. |
| 2016/0175238 A1 | 6/2016 | Shin et al. |
| 2016/0235649 A1 | 8/2016 | Streuli |
| 2017/0027832 A1 | 2/2017 | L'Oreal |
| 2017/0035667 A1 | 2/2017 | Benn et al. |
| 2017/0246094 A1 | 8/2017 | Dreher et al. |
| 2017/0273881 A1 | 9/2017 | Facheris et al. |
| 2018/0021600 A1* | 1/2018 | Kobayashi .............. A61K 8/49 8/405 |
| 2018/0042830 A1 | 2/2018 | Dreher et al. |
| 2018/0116930 A1 | 5/2018 | Degeorge et al. |
| 2018/0116942 A1 | 5/2018 | Mahadeshwar et al. |
| 2018/0177690 A1 | 6/2018 | Boulineau et al. |
| 2018/0280286 A1 | 10/2018 | Elsen-Wahrer et al. |
| 2018/0353404 A1 | 12/2018 | Nöcker et al. |
| 2019/0125650 A1 | 5/2019 | Lee et al. |
| 2019/0201309 A1* | 7/2019 | Machover .............. A61K 8/447 |
| 2021/0121385 A1 | 4/2021 | Muller et al. |
| 2021/0154116 A1 | 5/2021 | Lee et al. |
| 2021/0196600 A1 | 7/2021 | Shi et al. |
| 2021/0196606 A1 | 7/2021 | Shi et al. |
| 2021/0346261 A1 | 11/2021 | DeGeorge et al. |
| 2022/0062142 A1 | 3/2022 | Henry |

FOREIGN PATENT DOCUMENTS

| | | |
|---|---|---|
| DE | 1220969 B | 7/1966 |
| DE | 2359399 A1 | 6/1975 |
| DE | 3843892 A1 | 6/1990 |
| DE | 4133957 A1 | 4/1993 |
| DE | 19543988 A1 | 5/1997 |
| DE | 102009028593 A1 | 2/2011 |
| EP | 0080976 A1 | 6/1983 |
| EP | 0122324 A1 | 10/1984 |
| EP | 0714954 A2 | 6/1996 |
| EP | 0770375 A1 | 5/1997 |
| EP | 1810657 A1 | 7/2007 |
| EP | 2123250 A1 | 11/2009 |
| EP | 2301520 A2 | 3/2011 |
| EP | 2460511 A1 | 6/2012 |
| FR | 1492597 A | 8/1967 |
| FR | 1583363 A | 10/1969 |
| FR | 2162025 A | 7/1973 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2413907 A1 | 8/1979 |
| FR | 2505348 A1 | 11/1982 |
| FR | 2542997 A1 | 9/1984 |
| FR | 2733749 A1 | 11/1996 |
| FR | 2801308 A1 | 5/2001 |
| FR | 2886136 A1 | 12/2006 |
| FR | 2994088 A1 | 2/2014 |
| GB | 1026978 A | 4/1966 |
| GB | 1153196 A | 5/1969 |
| GB | 1546809 A | 5/1979 |
| JP | 63-154611 A | 6/1988 |
| JP | 02-019576 A | 1/1990 |
| JP | 05-163124 A | 6/1993 |
| JP | 08-198732 A | 8/1996 |
| JP | 2003-146844 A | 5/2003 |
| JP | 2005-255534 A | 9/2004 |
| JP | 2005-029486 A | 2/2005 |
| JP | 2015-086211 A | 5/2015 |
| KR | 10-2001-0039848 A | 7/2001 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 01/52005 A1 | 7/2001 |

(56) References Cited

FOREIGN PATENT DOCUMENTS

| WO | 2006/066674 A1 | 6/2006 |
|---|---|---|
| WO | 2006/106390 A2 | 10/2006 |
| WO | 2006/134051 A1 | 12/2006 |
| WO | 2012/157657 A1 | 11/2012 |
| WO | 2013/075892 A2 | 5/2013 |
| WO | 2013/136480 A1 | 9/2013 |
| WO | 2014/020148 A1 | 2/2014 |
| WO | 2014/020167 A2 | 2/2014 |
| WO | 2017/091796 A1 | 6/2017 |
| WO | 2017/207629 A1 | 12/2017 |
| WO | 2018/081399 A1 | 5/2018 |
| WO | 2018/183933 A1 | 10/2018 |
| WO | 2018/213652 A1 | 11/2018 |
| WO | 2019/133785 A1 | 7/2019 |
| WO | 2020/109859 A1 | 6/2020 |
| WO | 2021/138257 A1 | 7/2021 |
| WO | 2021138258 A1 | 7/2021 |

OTHER PUBLICATIONS

International Search Report and Written Opinion for counterpart Application No. PCT/US2021/039047, dated Nov. 2, 2021.
Mintel: "One-Touch Color," Hoyu, XP55820021, Record Id 4957439, dated Jul. 13, 2017.
Copending U.S. Appl. No. 17/853,663, entitled "Compositions for Imparting Color and Tone to the Hair," Inventor: Minli Shi, dated Jun. 29, 2022.
Copending U.S. Appl. No. 17/853,685, entitled "Compositions Containing Direct Dyes for Imparting Color and Tone to the Hair," Inventor: Minli Shi, dated Jun. 29, 2022.
French Search Report and Written Opinion for counterpart French Application No. 2109798, dated Jun. 7, 2022.
Mintel: "Whipped Hair Color," Hoyu, Record ID 7277945, XP05592777, Feb. 20, 2020.
Mintel: "Beard Color," Hoyu Indonesia, Record No. 8923967, XP055927764, Aug. 16, 2021.
Mintel: "Speedy Color Quick Hair Colourant for Men," Hoyu, Record No. 3774805, XP 055927781, Feb. 4, 2016.
French Search Report and Written Opinion for counterpart French Application No. 2109796, dated Jun. 3, 2022.
Third-Party Submission Under 37 C.F.R. 1.290 for U.S. Appl. No. 17/132,697, dated Jan. 27, 2021.
Non-Final Office Action for copending U.S. Appl. No. 17/101,206, dated Aug. 26, 2022.
International Preliminary Report on Patentability for counterpart Application No. PCT/US2020/067153, dated Jul. 14, 2022.
French Search Report and Written Opinion for counterpart Application No. FR2110537, dated Jun. 27, 2022.
First Examination Report for counterpart Indian Application No. 202217038673, dated Dec. 7, 2022, with translation.
First Examination Report for counterpart Indian Application No. 202217039846, dated Dec. 8, 2022, with translation.
French Search Report and Written Opinion for counterpart FR Application No. 2209666, dated May 9, 2023.
Non-Final Office Action for copending U.S. Appl. No. 17/853,685, dated Aug. 10, 2023.
Final Office Action for copending U.S. Appl. No. 17/379,405, dated Sep. 18, 2023.
Non-Final Office Action for copending U.S. Appl. No. 17/003,558, dated Oct. 13, 2023.
Final Office Action for copending U.S. Appl. No. 17/133,376, dated Apr. 5, 2023.
Non-Final Office Action for copending U.S. Appl. No. 17/133,376, dated Sep. 20, 2022.
Non-Final Office Action for copending U.S. Appl. No. 17/132,697, dated Sep. 20, 2022.
International Search Report and Written Opinion for counterpart Application No. PCT/US2017/058495, dated Jan. 5, 2018.
Non-Final Office Action for copending U.S. Appl. No. 15/339,035, dated Jan. 10, 2018.
Non-Final Office Action for copending U.S. Appl. No. 15/339,035, dated Oct. 5, 2018.
Final Office Action for copending U.S. Appl. No. 15/339,035, dated May 2, 2019.
Non-Final Office Action for copending U.S. Appl. No. 15/339,035, dated Aug. 20, 2019.
Final Office Action for copending U.S. Appl. No. 15/339,035, dated Apr. 10, 2020.
Non-Final Office Action for copending U.S. Appl. No. 15/339,035, dated Jun. 25, 2021.
Final Office Action for copending U.S. Appl. No. 15/339,035, dated Apr. 14, 2022.
Non-Final Office Action for copending U.S. Appl. No. 15/339,035, dated Oct. 27, 2022.
International Preliminary Report on Patentability for counterpart Application No. PCT/US2017/058495, mailed May 9, 2019.
Olaplex with relaxers, Olaplex™, pp. 1-2, Apr. 11, 2017, https://olaplex.es/olaplex-with-relaxers/.
Relaxers, Resource Library, Olaplex Education, pp. 1-2, Apr. 11, 2017, https://help.olaplex.com/detail/relaxers.
"Final Written Decision for U.S. Pat. No. 9,668,954 B2," Paper 78, Jul. 30, 2019, Case PGR2018-00025.
Non-Final Office Action for copending U.S. Appl. No. 15/801,425, mailed May 6, 2019.
Final Office Action for copending U.S. Appl. No. 15/801,425, mailed Nov. 12, 2019.
Non-Final Office Action for copending U.S. Appl. No. 15/801,425, mailed Jul. 24, 2020.
Third Party Submission for U.S. Appl. No. 17/379,405, dated May 10, 2022.
U.S. Appl. No. 61/994,709 "Hair Treatment Compositions and Methods," Inventores Pressly et al., May 16, 2014.
Final Office Action for copending U.S. Appl. No. 15/801,425, dated Feb. 26, 2021.
Non-Final Office Action for copending U.S. Appl. No. 15/801,425, dated Sep. 7, 2021.
Final Office Action for copending U.S. Appl. No. 15/801,425, dated May 31, 2022.
International Search Report and Written Opinion for counterpart Application No. PCT/US2021/047821, dated Feb. 7, 2022.
Database GNPD, "Oil Control Amino Acid Shampoo," Record ID No. 7915997, Mintel.
Database GNPD, "Illuminator Soap with Vitamin C," Record ID No. 4406687, Mintel.
Database GNPD, Anti Hair-Fall Fortifying Serum, Record ID No. 7242637, Mintel.
Database GNPD, "Elixium Plumping Anti-Aging Serumn," Record ID No. 6282723, Mintel.
Non-Final Office Action for copending U.S. Appl. No. 17/003,558, dated Jun. 23, 2022.
Non-Final Office Action for copending U.S. Appl. No. 17/003,558, dated Aug. 8, 2022.
International Preliminary Report on Patentability for counterpart Application No. PCT/US2021/047821, dated Feb. 28, 2023.
Non-Final Office Action for copending U.S. Appl. No. 17/379,405, dated Mar. 2, 2023.
Co-pending U.S. Appl. No. 17/878,001, entitled "Compositions and Methods for Altering The Color of Hair," Inventors: Shahid Nasser, filed Jul. 31, 2022.
Co-pending U.S. Appl. No. 17/877,999, entitled "Compositions and Methods for Altering the Color of Hair," Inventor: Jennifer Elie, filed Jul. 31, 2022.
French Search Report and Written Opinion for counterpart French Application No. FR2209427, dated Apr. 28, 2023.
Mintel: "Care & Moisture Color Permanent Hair Colour," Schwarzkopf and Henkel, Record ID 8511329, XP093042655, dated Feb. 24, 2021.
Mintel: "Colour and Protect Permanent Colouration," Schwarzkopf and Henkel, Record ID 8501329, XP093042658, dated Feb. 18, 2021.
Final Office Action for copending U.S. Appl. No. 17/101,206, dated May 26, 2023.

(56) References Cited

OTHER PUBLICATIONS

Final Office Action for copending U.S. Appl. No. 17/333,376, dated Apr. 5, 2023.
Final Office Action for copending U.S. Appl. No. 17/003,558, dated Jun. 26, 2023.
International Search Report and Written Opinion for counterpart Application No. PCT/US2023/029085, dated Oct. 19, 2023.
Non-Final Office Action for copending U.S. Appl. No. 17/853,663, dated Nov. 13, 2023.
International Preliminary Report on Patentability in PCT/US2022/035765, mailed Dec. 14, 2023, 8 pages.
Office Action in U.S. Appl. No. 17/878,001, mailed Feb. 20, 2024, 7 pages.
Non-Final Office Action for copending U.S. Appl. No. 17/877,999, dated Feb. 16, 2024.
Office Action in EP22747220.6, mailed Feb. 6, 2024, 3 pages.
Office Action in U.S. Appl. No. 17/003,558, mailed Mar. 25, 2024, 16 pages.
Non-Final Office Action for copending U.S. Appl. No. 17/379,405, dated Mar. 1, 2024.
Non-Final Office Action for copending U.S. Appl. No. 15/339,035, dated Apr. 22, 2024.
Non-Final Office Action for copending U.S. Appl. No. 17/101,206, dated Apr. 23, 2024.
Office Action in CN202080090709.9, mailed Feb. 27, 2024, 10 pages.

\* cited by examiner

COMPOSITIONS FOR IMPARTING COLOR AND TONE TO THE HAIR

CROSS REFERENCE TO RELATED APPLICATIONS

This application claims priority to U.S. Provisional Application No. 63/217,225, filed Jun. 30, 2021, and French Application No. FR 2109796, filed Sep. 17, 2021, the contents of both of which are incorporated by reference herein in their entireties.

TECHNICAL FIELD

The present disclosure generally relates to compositions and methods for imparting color and/or tone to the hair.

BACKGROUND

It is known that consumers desire to use cosmetic and care compositions that enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve chemical treatment of the hair.

The process of changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening, generally requires the use of compositions that comprise at least one oxidizing agent.

Lightening or lifting the color of the hair is typically evaluated by the variation in tone height before and after the application of a hair color toning composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

In general, hair lightening or color lifting compositions and hair dyeing compositions possess an alkalinity such that these compositions have a pH value of above 7, typically being at pH 9 and above, and generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. While this process is effective in altering the color of the hair, these chemical treatments can damage the hair fibers leading to decreased strength of the hair, as well as negatively affecting the sensorial properties of the hair, such as the smoothness, shine, and feel. Thus, in order to reduce or avoid these drawbacks, the use of new and additional components and treatment compositions for use before, during, or after, or as a complement to, processes for altering the color of the hair are needed.

However, the choice of such components or treatments could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can treat the hair, e.g. lift the color of hair and/or deposit color onto hair in an effective manner, while providing other cosmetic advantages such as shine, conditioning, fiber strength, and/or a healthy appearance to the hair, but avoiding or minimizing damage to the hair.

Another challenge to manufacturers of hair products that can change the color of hair is to find new dyes or colorants or new combinations of dyes or colorants that can either create new shades or color tones on hair or still achieve the same desired shades or color tones as existing products.

SUMMARY

The disclosure relates to compositions and methods for imparting color and/or tone and/or strength to the hair. The disclosure also relates to kits comprising compositions according to the disclosure.

The compositions comprise at least one amino acid, at least one carboxylic acid, monoethanolamine, and at least one hair coloring agent comprising an oxidation base chosen from toluene-2,5-diamine, acid salts thereof, or solvates thereof, and a coupler system comprising at least one coupler chosen from 2,4-diaminophenoxyethanol, meta-aminophenol, derivatives thereof, addition salts thereof, solvates thereof, solvates of salts thereof, or mixtures thereof. The methods comprise applying the compositions according to the disclosure to the hair.

In various embodiments, the hair color toning compositions according to the disclosure comprise: (a) at least one amino acid, (b) at least one carboxylic acid, (c) monoethanolamine, (d) at least one surfactant mixture comprising at least one amphoteric surfactant and at least one surfactant chosen from anionic or non-ionic surfactants, (e) at least one fatty compound, (f) at least one oxidation base chosen from toluene-2,5-diamine, acid salts thereof, or solvates thereof; (g) a coupler system comprising at least one coupler chosen from: (1) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof; and (h) at least one solvent. The compositions may have a pH ranging from about 7 to about 10.4.

In further embodiments, the hair color toning compositions according to the disclosure comprise (a) at least one amino acid, (b) at least one carboxylic acid, (c) monoethanolamine in an amount ranging from about 0.01% to about 3% by weight, relative to the weight of the composition, (d) at least one surfactant, (e) at least one fatty compound, (f) at least one oxidation base chosen from toluene-2,5-diamine, acid salts thereof, or solvates thereof, (g) a coupler system comprising at least one coupler chosen from: (1) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof, and (h) at least one solvent, wherein the composition has a pH ranging from about 7 to about 10.4.

In yet further embodiments, the hair color toning compositions according to the disclosure comprise (a) from about 0.1% to about 2% taurine by weight, relative to the weight of the composition, (b) from about 0.1% to about 3% citric acid by weight, relative to the weight of the composition, (c) from about 0.1% to about 3% monoethanolamine by weight, relative to the weight of the composition, (d) at least one surfactant, (e) at least one fatty compound chosen from C12-C22 fatty alcohols, (f) at least one oxidation base chosen from toluene-2,5-diamine, acid salts thereof, or solvates thereof, (g) a coupler system comprising at least one coupler chosen from: (1) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof, and (h) at least one solvent, wherein the composition has a pH ranging from about 8.5 to about 10.

The disclosure also relates to methods for altering the tone or color of the hair, the methods comprising mixing (i) a hair color toning composition comprising (a) at least one amino acid, (b) at least one carboxylic acid, (c) monoethanolamine, (d) a surfactant mixture comprising (i) at least one amphoteric surfactant and (ii) at least one surfactant chosen from anionic and non-ionic surfactants, (e) at least one fatty compound, (f) at least one oxidation base chosen from toluene-2,5-diamine, acid salts thereof, or solvates thereof, (g) a coupler system comprising at least one coupler chosen from: (1) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof, and (h) at least one solvent, wherein the hair color toning composition has a pH ranging from about 7 to about 10.4, with (ii) an oxidizing composition comprising at least one oxidizing agent, and applying the mixture to the hair, wherein the mixture has a pH ranging from about 6.0 to about 6.8.

In further embodiments, the disclosure relates to methods for altering the tone or color of the hair, the methods comprising mixing (i) a hair color toning composition comprising (a) at least one amino acid, (b) at least one carboxylic acid, (c) monoethanolamine, (d) at least one surfactant, (e) at least one fatty compound, (f) at least one oxidation base chosen from toluene-2,5-diamine, acid salts thereof, or solvates thereof, (g) a coupler system comprising at least one coupler chosen from: (1) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof, and (h) at least one solvent, wherein the monoethanolamine is present in an amount ranging from about 0.01% to about 3% by weight, relative to the weight of the composition, and the hair color toning composition has a pH ranging from about 7 to about 10.4, with (ii) an oxidizing composition comprising at least one oxidizing agent, and applying the mixture to the hair, wherein the mixture has a pH ranging from about 6.0 to about 6.8.

In further embodiments, the disclosure relates to methods for altering the tone or color of the hair, the methods comprising mixing (i) a hair color toning composition comprising (a) from about 0.1% to about 2% taurine by weight, relative to the weight of the hair color toning composition, (b) from about 0.1% to about 3% citric acid by weight, relative to the weight of the hair color toning composition, (c) from about 0.1% to about 3% monoethanolamine by weight, relative to the weight of the hair color toning composition, (d) at least one surfactant, (e) at least one fatty compound chosen from C12-C22 fatty alcohols, (f) at least one oxidation base chosen from toluene-2,5-diamine, acid salts thereof, or solvates thereof, (g) a coupler system comprising at least one coupler chosen from: (I) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof, and (h) at least one solvent, wherein the hair color toning composition has a pH ranging from about 8.5 to about 10, with (ii) an oxidizing composition comprising at least one oxidizing agent, and applying the mixture to the hair, wherein the mixture has a pH ranging from about 6.3 to about 6.8.

In still further embodiments, the disclosure relates to methods for altering the tone or color of the hair, the methods comprising mixing (i) a hair color toning composition comprising (a) from about 0.1% to about 2% of at least one amino acid, (b) at least one carboxylic acid, (c) from about 0.01% to about 3% of monoethanolamine, (d) at least one surfactant, (e) at least one fatty compound, (f) at least one oxidation base chosen from toluene-2,5-diamine, acid salts thereof, or solvates thereof, (g) a coupler system comprising at least one coupler chosen from: (1) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof, and (h) at least one solvent, wherein all amounts are by weight, relative to the weight of the composition, and the hair color toning composition has a pH ranging from about 7 to about 10.4, with (ii) an oxidizing composition comprising at least one oxidizing agent, and applying the mixture to the hair, wherein the mixture has a pH ranging from about 6.0 to about 6.8.

In further embodiments still, the disclosure relates to methods for altering the tone or color of the hair, the methods comprising mixing (i) a hair color toning composition comprising (a) from about 0.1% to about 2% taurine by weight, relative to the weight of the hair color toning composition, (b) from about 0.1% to about 3% citric acid by weight, relative to the weight of the hair color toning composition, (c) from about 0.1% to about 3% monoethanolamine by weight, relative to the weight of the hair color toning composition, (d) at least one surfactant, (e) at least one fatty compound chosen from C12-C22 fatty alcohols, (f) at least one oxidation base chosen from toluene-2,5-diamine, acid salts thereof, or solvates thereof, (g) a coupler system comprising at least one coupler chosen from: (I) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) (IV) mixtures thereof, and (h) at least one solvent, wherein the hair color toning composition has a pH ranging from about 8.5 to about 10, with (ii) an oxidizing composition comprising at least one oxidizing agent, and applying the mixture to the hair, wherein the mixture has a pH ranging from about 6.3 to about 6.8.

In various embodiments, the coupler system useful in compositions according to the disclosure comprises 2,4-diaminophenoxyethanol and meta-aminophenol (1-hydroxy-3-aminobenzene).

DETAILED DESCRIPTION

The disclosure relates to compositions for altering the color or tone of the hair, methods of using the compositions, and kits comprising the compositions.

I. Compositions

The compositions comprise at least one amino acid, at least one carboxylic acid, monoethanolamine, and at least one hair coloring agent comprising an oxidation base chosen from toluene-2,5-diamine, acid salts thereof, or solvates thereof, and a coupler system comprising at least one coupler chosen from 2,4-diaminophenoxyethanol, meta-aminophenol, derivatives thereof, addition salts thereof, solvates thereof, solvates of salts thereof, or mixtures thereof. The methods comprise applying the compositions according to the disclosure to the hair.

Amino Acids

The compositions according to the disclosure comprise at least one amino acid. As used herein, the term "amino acid" includes amino acids such as proteinogenic amino acids, amino sulfonic acids, and salts thereof.

Amino acids are organic compounds containing both a carboxylic acid group (—COOH) and an amino group (—NH$_2$). Amino sulfonic acids are organic compounds containing both a sulfonic acid group (—SO$_2$OH) and an amino group (—NH$_2$). Accordingly, the amino acids useful according to the disclosure may, in certain embodiments, be selected from compounds of Formula (I) or Formula (II):

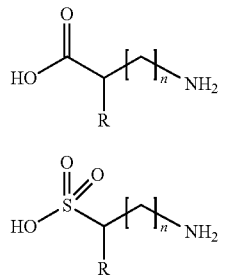

wherein:
R represents a hydrogen atom, a linear or branched, preferably linear, C$_1$-C$_5$ alkyl group, said alkyl group being optionally substituted with at least one group chosen from hydroxyl, —C(O)—OH, —S(O)$_2$—OH, —C(O)—O$^-$ and M$^+$, and S(O)$_2$—O$^-$ and M$^+$, with M$^+$ representing a cationic counter-ion such as an alkali metal, alkaline earth metal, or ammonium, and
n is 0 or 1.

The amino acids may be in their non-ionized form (I) and (II), or in their ionized or betaine form (I') and (II'):

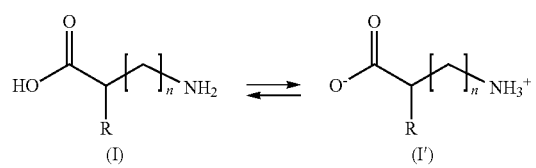

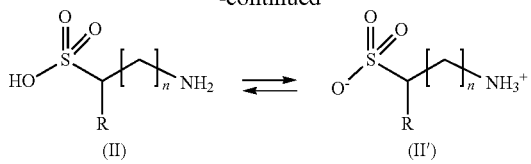

wherein:
R represents a hydrogen atom, a linear or branched, preferably linear, C$_1$-C$_5$ alkyl group, said alkyl group being optionally substituted with at least one group chosen from hydroxyl, —C(O)—OH, —S(O)$_2$—OH, —C(O)—O$^-$ and M$^+$, and S(O)$_2$—O$^-$ and M$^+$, with M$^+$ representing a cationic counter-ion such as an alkali metal, alkaline earth metal, or ammonium, and
n is 0 or 1.

The one or more amino acids may also be in their conjugate base form (Ib) and (IIb):

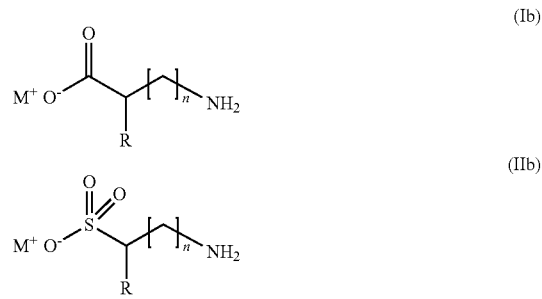

wherein:
R represents a hydrogen atom, a linear or branched, preferably linear, C$_1$-C$_5$ alkyl group, said alkyl group being optionally substituted with at least one group chosen from hydroxyl, —C(O)—OH, —S(O)$_2$—OH, —C(O)—O$^-$ and M$^+$, and S(O)$_2$—O$^-$ and M$^+$, with M$^+$ representing a cationic counter-ion such as an alkali metal, alkaline earth metal, or ammonium, and
n is 0 or 1.

Well-known amino acids include the twenty amino acids that form the proteins of living organisms (standard proteinogenic amino acids): alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. The amino acids of the instant disclosure, however, are not limited to the standard proteinogenic amino acids.

Non-limiting examples of amino sulfonic acids include aminomethane sulfonic acid, 2-aminoethane sulfonic acid (taurine), aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid, or mixtures thereof.

In some cases, charged amino acids may be used. Non-limiting examples of charged amino acids include arginine, lysine, aspartic acid, and glutamic acid. In some cases, polar amino acids are useful. Non-limiting examples of polar amino acids include glutamine, asparagine, histidine, serine, threonine, tyrosine, cysteine, methionine, and tryptophan.

In some cases, hydrophobic amino acids may be employed. Non-limiting examples of hydrophobic amino acids include alanine, isoleucine, leucine, phenylalanine, valine, proline, and glycine.

In certain exemplary embodiments, compositions according to the disclosure include at least one amino acid selected from the group consisting of glycine, alanine, serine, beta-alanine, taurine, sodium glycinate, sodium alaninate, sodium serinate, lithium beta-alanine, sodium taurate, or combinations thereof.

In further exemplary embodiments, compositions according to the disclosure include only amino acids or their salts, for example, those selected from the group consisting of aspartic acid, cysteine, glycine, lysine, methionine, proline, tyrosine, phenylalanine, carnitine, taurine, or salts thereof.

In various exemplary embodiments, the compositions include at least taurine. In further exemplary embodiments, the only amino acid in the composition is taurine. In still further exemplary embodiments, the compositions include at least glycine. In yet further exemplary embodiments, the only amino acid in the composition is glycine. In some exemplary embodiments, the compositions include both taurine and glycine.

The total amount of the at least one amino acid may range from about 0.01% to about 10% by weight, relative to the total weight of the hair color toning composition. For example, in some embodiments, the total amount of the at least one amino acid may range from about 0.05% to about 5%, such as about 0.1% to about 5%, about 0.1% to about 4%, about 0.1% to about 3%, about 0.1% to about 2.5%, about 0.1% to about 2.4%, about 0.1% to about 2.3%, about 0.1% to about 2.2%, about 0.1% to about 2.1%, about 0.1% to about 2%, about 0.1% to about 1.9%, about 0.1% to about 1.8%, about 0.1% to about 1.7%, about 0.1% to about 1.6%, about 0.1% to about 1.5%, about 0.1% to about 1.4%, about 0.1% to about 1.3%, about 0.1% to about 1.2%, about 0.1% to about 1.1%, about 0.1% to about 1%, about 0.1% to about 0.9%, about 0.1% to about 0.8%, about 0.1% to about 0.7%, about 0.1% to about 0.6%, about 0.1% to about 0.5%, about 0.1% to about 0.4%, or about 0.1% to about 0.3% by weight, relative to the total weight of the hair color toning composition. In other embodiments, the total amount of the at least one amino acid ranges from about 0.5% to about 5%, about 0.5% to about 4%, about 0.5% to about 3%, about 0.5% to about 2.5%, about 0.5% to about 2.4%, about 0.5% to about 2.3%, about 0.5% to about 2.2%, about 0.5% to about 2.1%, about 0.5% to about 2%, about 0.5% to about 1.9%, about 0.5% to about 1.8%, about 0.5% to about 1.7%, about 0.5% to about 1.6%, about 0.5% to about 1.5%, about 0.5% to about 1.4%, about 0.5% to about 1.3%, about 0.5% to about 1.2%, about 0.5% to about 1.1%, about 0.5% to about 1%, about 0.5% to about 0.9%, about 0.5% to about 0.8%, about 0.5% to about 0.7%, or about 0.5% to about 0.6% by weight, relative to the total weight of the hair color toning composition.

The total amount of the at least one amino acid may, in certain embodiments, be about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, or about 0.35% by weight, relative to the total weight of the hair color toning composition. In yet further embodiments, the total amount of the amino acid may be about 0.4%, about 0.5%, about 0.6%, about 0.7%, about 0.8%, about 0.9%, about 1%, about 1.1% about 1.2%, about 1.3%, about 1.4%, about 1.5%, about 1.6%, about 1.7% about 1.8%, about 1.9%, or about 2% by weight, relative to the total weight of the hair color toning composition. It is to be understood that any of the above-recited numbers may provide an upper or lower boundary for a range of the total amount of the at least one amino acid.

Carboxylic Acids

The hair color toning compositions include at least one carboxylic acid. As used herein, the term "carboxylic acid" includes salts of carboxylic acids. In certain embodiments, the carboxylic acids include non-polymeric mono, di, and/or tricarboxylic acid which are organic compounds having one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of mono-carboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, salt thereofs, or mixtures thereof. In some cases, the hair color toning compositions include at least lactic acid and/or a salt thereof.

Non-limiting examples of di-carboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, salts thereof, or mixtures thereof. In some cases, the hair color toning compositions include oxalic acid, malonic acid, malic acid, maleic acid, salts thereof, or mixtures thereof.

Non-limiting examples of tricarboxylic acids and salts thereof include citric acid, isocitric acid, aconitric acid, propane-1,2,3-tricarboxylic acid, benzene-1,3,5-tricarboxylic acid, salts thereof, or mixtures thereof. In some instances, the hair color toning compositions include at least citric acid and/or a salt thereof.

In one or more embodiments, the hair color toning composition comprises at least one carboxylic acid selected from the group consisting of oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof. In one exemplary embodiment, the compositions include at least citric acid. In a further embodiment, the only carboxylic acid in the composition is citric acid.

The total amount of the at least one carboxylic acid may range from about 0.01% to about 10% by weight, relative to the total weight of the hair color toning composition. For example, in some embodiments, the total amount of the at least one carboxylic acid may range from about 0.05% to about 5%, such as about 0.1% to about 5%, about 0.1% to about 4%, about 0.1% to about 3%, about 0.1% to about 2.5%, about 0.1% to about 2.4%, about 0.1% to about 2.3%, about 0.1% to about 2.2%, about 0.1% to about 2.1%, about 0.1% to about 2%, about 0.1% to about 1.9%, about 0.1% to about 1.8%, about 0.1% to about 1.7%, about 0.1% to about 1.6%, about 0.1% to about 1.5%, about 0.1% to about 1.4%, about 0.1% to about 1.3%, about 0.1% to about 1.2%, about 0.1% to about 1.1%, about 0.1% to about 1%, about 0.1% to about 0.9%, about 0.1% to about 0.8%, about 0.1% to about 0.7%, about 0.1% to about 0.6%, about 0.1% to about 0.5%, about 0.1% to about 0.4%, or about 0.1% to about 0.3% by weight, relative to the total weight of the hair color toning composition. In other embodiments, the total amount of the at least one carboxylic acid ranges from about 0.5% to about 5%, about 0.5% to about 4%, about 0.5% to about 3%, about 0.5% to about 2.5%, about 0.5% to about 2.4%, about 0.5% to about 2.3%, about 0.5% to about 2.2%, about 0.5% to about 2.1%, about 0.5% to about 2%, about 0.5% to about 1.9%, about 0.5% to about 1.8%, about 0.5% to about 1.7%, about 0.5% to about 1.6%, about 0.5% to about 1.5%, about 0.5% to about 1.4%, about 0.5% to about 1.3%, about 0.5% to about 1.2%, about 0.5% to about 1.1%, about 0.5% to about 1%, about 0.5% to about 0.9%, about 0.5% to about 0.8%, about 0.5% to about 0.7%, or about 0.5% to about 0.6% by weight, relative to the total weight of the hair color toning composition.

The total amount of the at least one carboxylic acid may, in certain embodiments, be about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.4%, about 0.41%, about 0.42%, about 0.43%, about 0.44%, about 0.45%, about 0.46%, about 0.47%, about 0.48%, about 0.49%, or about 0.5% by weight, relative to the total weight of the hair color toning composition. It is to be understood that any of the above-recited numbers may provide an upper or lower boundary for a range of the total amount of the at least one carboxylic acid.

Monoethanolamine

The hair color toning compositions according to the disclosure comprise monoethanolamine. The monoethanolamine may be present in the composition in an amount up to about 10%, such from about 0.001% up to about 10%, or from about 0.01% up to about 5%, up to about 4%, up to about 3.9%, up to about 3.8%, up to about 3.7%, up to about 3.6%, up to about 3.5%, up to about 3.4%, up to about 3.3%, up to about 3.2%, up to about 3.1%, up to about 3%, up to about 2.9%, up to about 2.8%, up to about 2.7%, up to about 2.6%, up to about 2.5%, up to about 2.4%, up to about 2.3%, up to about 2.2%, up to about 2.1%, up to about 2.0%, up to about 1.9%, up to about 1.8%, up to about 1.7%, up to about 1.6%, up to about 1.5%, up to about 1.4%, up to about 1.3%, up to about 1.2%, up to about 1.1%, up to about 1%, up to about 0.9%, up to about 0.8%, up to about 0.7%, up to about 0.6%, up to about 0.5%, up to about 0.4%, up to about 0.3%, up to about 0.2%, up to about 0.1%, or up to about 0.05% by weight, based on the weight of the composition. By way of example, the monoethanolamine may be present in an amount of about 0.1%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, or about 3.5% by weight, based on the weight of the composition.

Fatty Compounds

Fatty compounds (also referred to interchangeably as "fatty substances") may be included in one or more embodiments of the invention. In some embodiments, two or more fatty compounds may be included. In further embodiments, such fatty compounds may be chosen from fatty compounds other than a fatty acid. As used herein, "fatty compound" means an organic compound insoluble in water at normal temperature (25° C.) and at atmospheric pressure (760 mmHg) (solubility below 5% and such as below 1% and further such as below 0.1%). Fatty compounds have in their structure a chain of at least two siloxane groups or at least one hydrocarbon chain having at least 6 carbon atoms. Moreover, fatty compounds are generally soluble in organic solvents in the same conditions of temperature and pressure, for example in chloroform, ethanol, benzene or decamethylcyclopentasiloxane.

Fatty compounds are, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4).

If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Non-limiting examples of non-silicone oils usable in the composition of the disclosure, include: esters of a glycerol oligomer, in particular diglycerol esters, especially condensates of adipic acid and of glycerol, for which a portion of the hydroxyl groups of the glycerols has reacted with a mixture of fatty acids, such as stearic acid, capric acid, isostearic acid and 12-hydroxystearic acid, such as in particular those sold under the brand name Softisan 649 by Sasol; arachidyl propionate, sold under the brand name Waxenol 801 by Alzol; fatty acid triglycerides and their derivatives; pentaerythritol esters; esters of dimer diol and dimer diacid, if appropriate esterified on their free alcohol or acid functional group(s) by acid or alcohol radicals, in particular dimer dilinoleate esters; such esters can be chosen in particular from esters with the following INCI nomenclature: bis-behenyl/isostearyl/phytosteryl dimer dilinoleyl dimer dilinoleate (Plandool G), phytosteryl isostearyl dimer dilinoleate (Lusplan PI-DA or Lusplan PHY/IS-DA), phytosteryl/isostearyl/cetyl/stearyl/behenyl dimer dilinoleate (Plandool H or Plandool S), and their mixtures; mango butter, such as that sold under the reference Lipex 203 by AarhusKarlshamn; hydrogenated soybean oil, hydrogenated coconut oil, hydrogenated rapeseed oil or mixtures of hydrogenated vegetable oils, such as the soybean, coconut, palm and rapeseed hydrogenated vegetable oil mixture, for example the mixture sold under the reference Akogel® by AarhusKarlshamn (INCI name: Hydrogenated Vegetable Oil); shea butter, in particular that having the INCI name Butyrospermum Parkii Butter, such as that sold under the reference Sheasoft® by AarhusKarlshamn; cocoa butter, in particular that which is sold under the name CT Cocoa Butter Deodorized by Dutch Cocoa BV or that which is sold under the name Beurre De Cacao NCB HD703 758 by Barry Callebaut; shorea butter, in particular that which is sold under the name Dub Shorea T by Stearinerie Dubois; and their mixtures.

According to one exemplary embodiment, the fatty compound is chosen from hydrogenated vegetable oil, shea butter, cocoa butter, shorea butter, a soybean, coconut, palm and rapeseed hydrogenated vegetable oil mixture, or their mixtures, and more particularly those referenced above.

Non-limiting examples of non-silicone oils usable in the composition of the disclosure, include: hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; non-afluoro-methoxybutane and nonafluoroethoxyisobutane; derivatives of perfluoromorpholine, such as 4-trifluoromethyl perfluoromorpholine sold under the name "PF 5052®" by the 3M Company. The non-silicone oils may be employed in an amount of from about 0.5% to about 5% by weight, such as from about 1% to about 5.5% by weight, and further such as from about 1.5% to about 4% by weight, based on the total weight of the hair color composition of the present invention, including increments and ranges therein there between.

The total amount of the non-silicone oils in the present invention may be employed in an amount ranging from about 0.5, 0.6, 0.7, 0.8, 0.9, 1, 2, 3, 4, to about 5 percent by weight, including increments and ranges therein there between.

As used herein, "fatty alcohol" refers to any alcohol with a carbon chain of C5 or greater, such as, for example, C8 or greater, C10 or greater, and C12 or greater. The at least one fatty alcohol may be chosen from, for example, C9-C11 alcohols, C12-C13 alcohols, C12-C15 alcohols, C12-C16 alcohols, C14-C15 alcohols, C12-C22 alcohols, arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol.

As used herein, "alkoxylated fatty alcohol" refers to any fatty alcohol with a carbon chain of C5 or greater, as defined above, further comprising at least one alkoxy group. For example, the at least one alkoxylated fatty alcohol may have a carbon chain of C8 or greater, C10 or greater, and C12 or greater. Further, for example, the at least one alkoxylated fatty alcohol may be chosen from alkoxylated polymers (including co-, ter- and homo-polymers) derived from alcohols such as glycerol (e.g. polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether.

Non-limiting examples of the at least one alkoxylated fatty alcohol include ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, cetearel:h-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, lauretih-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C11-C15 pareth-20, C12-C15 pareth-9, C12-C15 pareth-12, and C22-C24 pareth-33.

The fatty alcohols useful according to the disclosure include, but are not limited to, non-alkoxylated, saturated or unsaturated, linear or branched, and have from 6 to 30 carbon atoms and more particularly from 8 to 30 carbon atoms; For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used in the composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched C1-C26 aliphatic mono- or polyacids and of saturated or unsaturated, linear or branched C1-C26 aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of C4-C22 di- or tricarboxylic acids and of C1-C22 alcohols and the esters of mono-, di-, or tricarboxylic acids and of C2-C26 di-, tri-, tetra-, or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; glycol distearates; and polyethylene glycol distearates.

Among the esters mentioned above, non-limiting exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate, dioctyl malate, hexyl laurate, 2-hexyldecyl laurate, isononyl isononanate, cetyl octanoate, or mixtures thereof.

The composition can also comprise, as fatty esters, esters and di-esters of sugars of C6-C30, such as C12-C22, fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides, or polysaccharides.

As suitable sugars, non-limiting examples include sucrose, glucose, galactose, ribose, fucose, maltose, fructose, mannose, arabinose, xylose, lactose, or their derivatives, for example alkylated derivatives, such as methylated derivatives, e.g. methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$, fatty acids. If they are unsaturated, these compounds can have, for example, one to three, conjugated or unconjugated, carbon-carbon double bonds.

The esters according to some embodiments can be chosen from mono-, di-, tri-, and tetra-esters, polyesters, or mixtures thereof. These esters can be, for example, oleate, laurate, palmitate, myristate, behenate, cocoate, stearate, linoleate, linolenate, caprate, arachidonates, or mixtures thereof, such as the oleo-palmitate, oleo-stearate, or palmito-stearate mixed esters. For example, the mono- and di-esters can be used, for example mono- or di-oleate, stearate, behenate, oleopalmitate, linoleate, linolenate, oleostearate, of sucrose, of glucose, or of methylglucose. Non-limiting mention can be made of the product sold under the name GLUCATE® DO by the company Amerchol, which is a dioleate of methylglucose.

Exemplary esters or of mixtures of esters of sugar of fatty acid include: the products sold under the names F160, F140, F110, F90, F70, or SL40 by the company Crodesta, denoting respectively the palmitostearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the mono-laurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

Mixtures of two or more, for example three or more, four or more, etc., of the foregoing, may be chosen.

Surfactants

The hair color toning compositions comprise one or more surfactants selected from anionic surfactants, nonionic surfactants, amphoteric surfactants, or mixtures thereof. In some exemplary embodiments, the surfactant is a surfactant mixture comprising at least one amphoteric surfactant and at least one anionic surfactant. In further embodiments, the surfactant is a surfactant mixture comprising at least one amphoteric surfactant and at least one non-ionic surfactant. In yet further embodiments, the surfactant is a surfactant mixture comprising at least one non-ionic surfactant and at least one anionic surfactant.

The total amount of the one or more surfactants included in the hair color toning compositions can vary, especially depending on the type of hair color toning composition in with they are contained. The total amount of the one or more surfactants typically ranges from about 0.1% to about 60% by weight, relative to the total weight of the hair color toning composition, including all ranges and subranges therebetween. In some cases, the total amount of the one or more surfactants ranges from about 0.1% to about 50%, about 0.1% to about 45%, about 0.1% to about 40%, about 0.1% to about 35%, about 0.1% to about 30%, about 0.1 to about 25%, about 0.1 to about 20%, about 0.1 to about 15%, about 0.1 to about 10%, about 0.1 to about 5%, about 0.5 to about 40%, about 0.5 to about 35%, about 0.5 to about 30%, about 0.5 to about 25%, about 0.5 to about 20%, about 0.5 to about 15%, about 0.5 to about 10%, about 0.5 to about 5%, about 1% to about 40%, about 1% to about 30%, about 1% to about 20%, about 1% to about 15%, about 1% to about 10%, or about 1% to about 5% by weight, relative to the total weight of the hair treatment composition. In further embodiments, the total amount of the one or more surfactants ranges from about 15% to about 55%, about 15% to about 50%, about 15% to about 45%, about 15% to about 40%, about 15% to about 35%, about 15% to about 30%, about 15% to about 25%, about 20% to about 55%, about 20% to about 50%, about 20% to about 45%, about 20% to about 40%, about 20% to about 35%, about 20% to about 30%, about 20% to about 25%, about 25% to about 55%, about 25% to about 50%, about 25% to about 45%, about 25% to about 40%, about 25% to about 35%, about 25% to about 30%, 30% to about 55%, about 30% to about 50%, about 30% to about 45%, about 30% to about 40%, about 30% to about 35%, about 35% to about 55%, about 35% to about 50%, about 35% to about 45%, about 35% to about 40%, about 40% to about 55%, about 40% to about 50%, or about 40% to about 45% by weight, relative to the total weight of the hair color toning composition.

Anionic Surfactants

The term "anionic surfactant" means a surfactant comprising, as ionic or ionizable groups, only anionic groups. These anionic groups may optionally be chosen from, for example, the groups —$CO_2H$, —$CO_2^-$, —$SO_3H$, —$SO_3^-$, —$OSO_3H$, —$OSO_3^-$, —$O_2PO_2H$, —$O_2PO_2H$ or —$O_2PO_2^{2-}$.

The hair color toning compositions may include one or more anionic surfactants. Non-limiting examples of anionic surfactants include alkyl sulfates, alkyl ether sulfates, acyl isethionates, acyl glycinates, acyl taurates, acyl amino acids, acyl sarcosinates, sulfosuccinates, sulfonates, or mixtures thereof, wherein the alkyl and acyl groups of all these compounds optionally comprise from 6 to 24 carbon atoms. In at least some embodiments, anionic sulfate surfactants may be excluded from the one or more anionic surfactants. In such cases, the one or more anionic surfactants may be selected from the group consisting of acyl isethionates, acyl glycinates, acyl taurates, acyl amino acids, acyl sarcosinates, sulfosuccinates, sulfonates, or mixtures thereof, wherein the alkyl and acyl groups of all these compounds optionally comprise from 6 to 24 carbon atoms.

The total amount of the one or more anionic surfactants may be about 1% to about 40% by weight (inclusive of endpoints), relative to the total weight of the hair color toning composition, including all ranges and subranges therebetween. Furthermore, the total amount of the one or more anionic surfactants may range from about 1% to about 35%, from about 1% to about 30%, from about 5% to about 40%, from about 5% to about 25%, from about 5% to about 30%, from about 10% to about 40%, from about 10% to about 35%, or from about 15% to about 40%, inclusive of all endpoints.

The anionic surfactant(s) that may be used include, for example, alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates, and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units. By way of non-limiting example, the anionic surfactant may be chosen from sodium olefin sulfonates, e.g. sodium C14-C16 olefin sulfonate.

The salts of $C_6$-$C_{24}$ alkyl monoesters of polyglycoside-polycarboxylic acids may be chosen from, for example, $C_6$-$C_{24}$ alkyl polyglycoside-citrates, $C_6$-$C_{24}$ alkyl polyglycoside-tartrates, $C_6$-$C_{24}$ alkyl polyglycoside-sulfo succinates, or mixtures thereof.

When the anionic surfactant(s) are in salt form, they may be chosen especially from alkali metal salts such as the sodium salt or the potassium salt, ammonium salts, amine salts and in particular amino alcohol salts, or alkaline-earth metal salts such as the magnesium salt.

Examples of amino alcohol salts that may especially be mentioned include monoethanolamine, diethanolamine, or triethanolamine salts, monoisopropanolamine, diisopropanolamine, or triisopropanolamine salts, 2-amino-2-methyl-1-propanol salts, 2-amino-2-methyl-1,3-propanediol salts, and tris(hydroxymethyl)aminomethane salts. Alkali metal or alkaline-earth metal salts and in particular the sodium or magnesium salts may be used.

Use is also made of ($C_6$-$C_{24}$)alkyl sulfates or ($C_6$-$C_{24}$) alkyl ether sulfates, which are optionally ethoxylated, comprising from 2 to 50 ethylene oxide units, or mixtures thereof, in particular in the form of alkali metal salts or alkaline-earth metal salts, ammonium salts or amino alcohol salts. More preferentially, the anionic surfactant(s) are chosen from ($C_{10}$-$C_{20}$)alkyl ether sulfates, and in particular sodium lauryl ether sulfate.

Non-Ionic Surfactants

Non-ionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference.

The total amount of the one or more non-ionic surfactants may be about 1% to about 40% by weight, relative to the total weight of the hair color toning composition, including all ranges and subranges therebetween. Furthermore, the total amount of the one or more non-ionic surfactants may be about 1% to about 35%, about 1% to about 30%, about 5% to about 40%, about 5% to about 25%, about 5% to about 30%, about 10% to about 40%, about 10% to about 35%, or about 15% to about 40% by weight, relative to the total weight of the hair color toning composition.

The non-ionic surfactant can be, for example, selected from alcohols, alpha-diols, alkylphenols or esters of fatty acids, these compounds optionally being ethoxylated, propoxylated, or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may, for example, be chosen from polyoxyalkylenated or polyglycerolated nonionic surfactants. The oxyalkylene units are more particularly oxyethylene or oxypropylene units, or mixtures thereof, and may in some embodiments be oxyethylene units.

Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

As examples of polyglycerolated nonionic surfactants, polyglycerolated $C_8$-$C_{40}$ alcohols may be used. In some embodiments, the polyglycerolated $C_8$-$C_{40}$ alcohols correspond to the following formula:

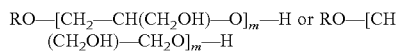

RO—[CH$_2$—CH(CH$_2$OH)—O]$_m$—H or RO—[CH(CH$_2$OH)—CH$_2$O]$_m$—H in which R represents a linear or branched $C_8$-$C_{40}$ and optionally $C_8$-$C_{30}$ alkyl or alkenyl radical, and m represents a number ranging from 1 to 30, for example from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

According to some embodiments, the nonionic surfactant may be selected from esters of polyols with fatty acids with a saturated or unsaturated chain containing for example from 8 to 24 carbon atoms, for example 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, e.g. $C_{12}$-$C_{22}$, fatty acid or acids and alkoxylated derivatives thereof, for example with a number of alkyleneoxide of from 10 to 200, such as from 10 to 100; polyethylene glycol esters of a $C_8$-$C_{24}$, e.g. $C_{12}$-$C_{22}$, fatty acid or acids and alkoxylated derivatives thereof, for example with a number of alkyleneoxide of from 10 to 200, e.g. from 10 to 100; sorbitol esters of a $C_8$-$C_{24}$, e.g. $C_{12}$-$C_{22}$, fatty acid or acids and alkoxylated derivatives thereof, for example with a number of alkyleneoxide of from 10 to 200, e.g. from 10 to 100; sugar (sucrose, glucose, alkylglycose) esters of a $C_8$-$C_{24}$, e.g. $C_{12}$-$C_{22}$, fatty acid or acids and alkoxylated derivatives thereof, for example with a number of alkyleneoxide of from 10 to 200, e.g. from 10 to 100; ethers of fatty alcohols; ethers of sugar and a $C_8$-$C_{24}$, e.g. $C_{12}$-$C_{22}$, fatty alcohol or alcohols; or mixtures thereof.

In some embodiments, the nonionic surfactant may be a nonionic surfactant with an HLB of 18.0 or less, such as from 4.0 to 18.0, from 6.0 to 15.0, or from 9.0 to 13.0. The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

In some embodiments, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, or mixtures thereof.

Amphoteric Surfactants

Compositions according to the disclosure may comprise at least one amphoteric surfactant. Non-limiting examples of amphoteric surfactants useful in the compositions include, for example, optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C8-C20)alkylbetaines, sulfobetaines, (C8-C20)alkylsulfobetaines, (C8-C20)alkylamido(C1-C6)alkylbetaines, such as cocamidopropylbetaine, and (C8-C20)alkylamido(C1-C6)alkylsulfobetaines, and mixtures thereof. For example, mention may be made of compounds classified under the INCI names sodium cocoamphoacetate, sodium lauroamphoacetate, sodium caproamphoacetate, and sodium capryloamphoacetate.

Other compounds that may be chosen include disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Examples that may be mentioned include the cocoamphodiacetate sold by the company Rhodia under the trade name Miranol®, C2M Concentrate, the sodium cocoamphoacetate sold under the trade name Miranol Ultra C 32, and the product sold by the company Chimex under the trade name CHIMEXANE HA. In certain exemplary embodiments, the amphoteric surfactants are chosen from (C8-C20) alkylbetaines such as the one known under the INCI names coco-betaine, (C8-C20)alkylamido(C1-C6)alkylbetaines such as the one known under the INCI name cocamidopropylbetaine, or mixtures thereof. In one embodiment, the amphoteric surfactant is coco-betaine.

The compositions according to the invention may, in various embodiments, comprise amphoteric surfactants in an amount ranging from about 0.1% to about 10%, such as from about 0.5% to about 8%, from about 1% to about 5%, or from about 1% to about 3% by weight, relative to the total weight of the composition.

Hair Coloring Agents

The compositions according to the disclosure comprise a hair coloring agent, i.e., an oxidative dye comprising at least one oxidation base chosen from toluene-2,5-diamine, acid salts thereof, or solvates thereof, and a coupler system comprising at least one coupler chosen from: (1) 2,4-diaminophenoxyethanol, derivatives thereof, addition salts thereof, solvates thereof, or solvates of salts thereof; (II) meta-aminophenol (1-hydroxy-3-aminobenzene), derivatives thereof, addition salts thereof, solvates thereof, or solvates of salts thereof; or (III) mixtures thereof. When the composition comprises a mixture (III) of two or more of couplers (I)-(II), it may be referred to as a "coupler system" for convenience, but it is to be understood that a composition comprising only one coupler may also be referred to as a coupler system, without intending to be limiting of the scope of the disclosure.

In various embodiments, the compositions according to the disclosure may comprise additional oxidative dyes, the oxidative dyes being generally chosen from one or more oxidation bases optionally combined with one or more couplers. By way of example, the additional oxidation bases (other than toluene-2,5-diamine, acid salts thereof, or solvates thereof), may be chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, 2-chloropara-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis((β-hydroxyethyl)-para-phenylenediamine, 4-N,N-bis((β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(R-hydroxyethyl)-para-phenylenediamine, N—(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(R-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis((β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(p-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases can include the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-R-hydroxyethoxy-3-amino-pyrazolo[1,5-a]pyridine; 2-(4-diméthylpyperazinium-1-yl)-3-aminopyrazolo[1,5-a]pyridine; and the addition salts thereof.

More particularly, oxidation bases can be selected from 3-aminopyrazolo-[1,5-a]-pyridines, which may be optionally substituted on carbon atom 2 by: (a) one (di)($C_1$-$C_6$) (alkyl)amino group wherein said alkyl group can be substituted by at least one hydroxy, amino, imidazolium group; (b) one heterocycloalkyl group containing from 5 to 7 members chain, and from 1 to 3 heteroatomes, potentially cationic, potentially substituted by one or more ($C_1$-$C_6$)alkyl, such as di($C_1$-$C_4$)alkylpiperazinium; or (c) one ($C_1$-$C_6$)alkoxy potentially substituted by one or more hydroxy groups such as α-hydroxyalkoxy, or the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methyl-pyrazole, 4,5-diamino-1-(p-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(p-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(p-hydroxyethyl)amino-1-methylpyrazole, and the addition salts thereof. 4,5-Diamino-1-(R-methoxyethyl)pyrazole may also be used. A 4,5-diaminopyrazole can be used in certain embodiments, for example 4,5-diamino-1-(p-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one.

4,5-Diamino-1-(R-hydroxyethyl)pyrazole and/or 2,3-diamino-6,7-dihydro-1H,5H-pyrazolo[1,2-a]pyrazol-1-one and/or a salt thereof may, in various embodiments, be used as heterocyclic bases.

Compositions and/or systems according to embodiments of the disclosure may optionally further comprise additional couplers advantageously chosen from those conventionally used in the dyeing or coloring of keratinous substrates. These are in addition to 2,4-diaminophenoxyethanol, meta-aminophenol, derivatives thereof, addition salts thereof, solvates thereof, or solvates of salts thereof.

Among these additional couplers, mention may be made especially of meta-phenylenediamines, meta-aminophenols, meta-diphenols, naphthalene-based couplers and heterocyclic couplers, and also the addition salts thereof.

Mention may be made, for example, of 4-amino-2-hydroxy toluene, 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methylbenzene, 4-chloro-1,3-dihydroxybenzene, 2,4-diamino-1-(β-hydroxy-ethyloxy)benzene, 2-amino-4-(β-hydroxyethylamino)-1-methoxybenzene, 1,3-diamino-benzene, 1,3-bis(2,4-diaminophenoxy)propane, 3-ureidoaniline, 3-ureido-1-dimethyl-aminobenzene, sesamol, 1-β-hydroxyethylamino-3,4-methylenedioxybenzene, ca-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]-benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) may be present in an amount ranging from about 0.001% to 10% by weight, such as from about 0.001% to 6% by weight, relative to the total weight of the system or composition in which it is present.

The coupler(s), if they are present, may be present in an amount ranging from about 0.001% to 10% by weight, such as from about 0.001% to 6% by weight, relative to the total weight of the system or composition in which it is present.

Compositions according to embodiments of the disclosure may optionally comprise one or more synthetic or natural direct dyes, for example chosen from cationic, anionic, or nonionic species, in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

According to various embodiments, direct dyes that can be included are cationic direct dyes. Mention may be made of the hydrazono cationic dyes of formulas (Va) and (V'a), the azo cationic dyes (VIa) and (VI'a), and the diazo cationic dyes (VIIa) below:

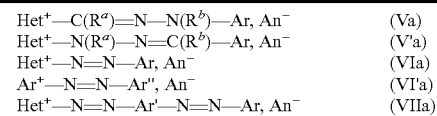

| | |
|---|---|
| Het$^+$—C(R$^a$)=N—N(R$^b$)—Ar, An$^-$ | (Va) |
| Het$^+$—N(R$^a$)—N=C(R$^b$)—Ar, An$^-$ | (V'a) |
| Het$^+$—N=N—Ar, An$^-$ | (VIa) |
| Ar$^+$—N=N—Ar'', An$^-$ | (VI'a) |
| Het$^+$—N=N—Ar'—N=N—Ar, An$^-$ | (VIIa) | in which formulas (Va), (V'a), (VIa), (VI'a), and (VIIa):
Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;
Ar$^+$ representing an aryl radical, such as phenyl or naphthyl, bearing an exocyclic cationic charge, preferentially ammonium, particularly tri($C_1$-$C_8$)alkylammonium such as trimethylammonium;
Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;
Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;
Ar'' is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;
R$^a$ and R$^b$, which may be identical or different, represent a hydrogen atom or a group ($C_1$-$C_8$)alkyl, which is optionally substituted, preferentially with a hydroxyl group; or alternatively the substituent R$^a$ with a substituent of Het$^+$ and/or R$^b$ with a substituent of Ar and/or R$^a$ with R$^b$ form, together with the atoms that bear them, a (hetero)cycloalkyl; particularly, R$^a$ and R$^b$ represent a hydrogen atom or a group (C₁-C₄)alkyl, which is optionally substituted with a hydroxyl group; and An⁻ represents an anionic counter-ion such as mesylate or halide.

For example, mention may be made of the azo and hydrazono cationic dyes bearing an endocyclic cationic charge of formulae (Va), (V'a), and (VIa) as defined previously, such as those of formulae (Va), (V'a), and (VIa) derived from the dyes described in patent applications WO 95/15144, WO 95/01772 and EP-714954.

Optionally, the cationic part is derived from the following derivatives:

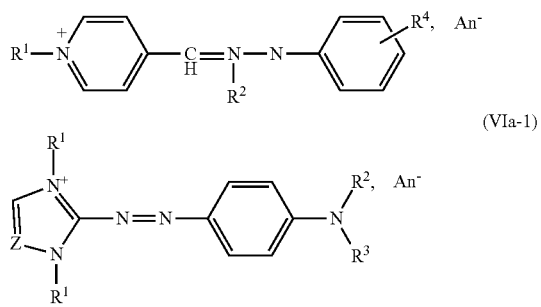

with:
- R¹ representing a (C₁-C₄) alkyl group such as methyl;
- R² and R³, which are identical or different, represent a hydrogen atom or a (C₁-C₄)alkyl group, such as methyl; and
- R⁴ represents a hydrogen atom or an electron-donating group such as optionally substituted (C₁-C₈)alkyl, optionally substituted (C₁-C₈)alkoxy, or (di)(C₁-C₈)(alkyl)amino optionally substituted on the alkyl group(s) with a hydroxyl group; particularly, R⁴ is a hydrogen atom,
- Z represents a CH group or a nitrogen atom, preferentially CH;
- An⁻ represents an anionic counter-ion such as mesylate or halide.

The dyes of formulae (Va-1) and (Via-1) can be chosen from Basic Red 51, Basic Yellow 87, and Basic Orange 31, or derivatives thereof:

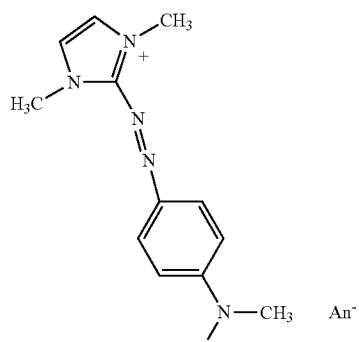

Basic Red 51

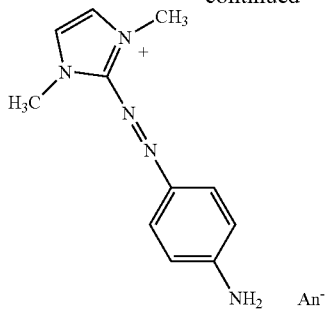

Basic Orange 31

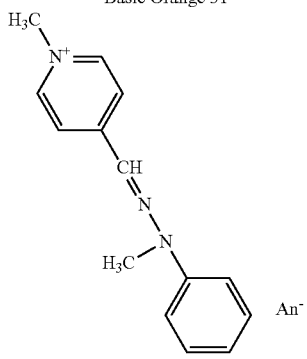

Basic Yellow 87

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin, and orceins. Extracts or decoctions containing these natural dyes and in particular henna-based poultices or extracts may also be used.

When they are present, the one or more direct dyes more represent from about 0.001% to 10% by weight, such as from about 0.005% to 5% by weight, of the total weight of the system or composition comprising the system in which it is present.

Solvent

The hair color toning compositions according to the disclosure comprise a solvent. The solvent may be chosen from water, non-aqueous solvents, or combinations thereof. The solvent may be present in the hair color toning composition in an amount ranging from about 10% to about 95% by weight, relative to the total weight of the hair color toning composition. For example, the total amount of solvent may range from about 20% to about 90%, about 20% to about 85%, about 20% to 75%, about 20% to about 70%, about 20% to about 65%, about 20% to about 60%, about 20% to about 55%, about 30% to about 90%, about 30% to about 85%, about 30% to 75%, about 30% to 70%, about 30% to about 65%, about 30% to about 60%, about 30% to about 55%, about 40% to about 90%, about 40% to about 85%, about 40% to 75%, about 40% to 70%, about 40% to about 65%, about 40% to about 60%, about 40% to about 55%, about 50% to about 90%, about 50% to about 85%, about 50% to 75%, about 50% to 70%, about 50% to about 65%, or about 50% to about 60% by weight, relative to the total weight of the hair color toning composition.

In some embodiments, the solvent comprises, consists essentially of, or consists of water. The total amount of water in the hair color toning compositions may vary depending on the type of composition and the desired consistency, viscosity, etc. In some embodiments, the total amount of water is about 10% to about 95% by weight, relative to the total weight of the hair color toning composition, including all ranges and subranges therebetween. For example, the total amount of water may be about 10% to about 90%, about 10% to about 85%, about 10% to 75%, about 10% to 70%, about 10% to about 65%, about 10% to about 60%, about 10% to about 55%, about 10% to about 50%, about 10% to about 45%, about 10% to about 40%, about 10% to about 35%, about 10% to about 30%, or about 15% to about 30% by weight, relative to the total weight of the hair color toning composition. It may, in at least certain embodiments, be desirable to include water in an amount less than about 60%, less than about 55%, less than about 50%, less than about 45%, less than about 40%, less than about 35%, less than about 30%, less than about 25%, or less than about 20% by weight, relative to the total weight of the hair color toning composition. For example, the water may be present in an amount ranging from about 1% to about 55%, about 1% to about 50%, about 1% to about 45%, about 1% to about 40%, about 1% to about 35%, about 1% to about 30%, about 1% to about 25%, about 1% to about 20%, 5% to about 55%, about 5% to about 50%, about 5% to about 45%, about 5% to about 40%, about 5% to about 35%, about 5% to about 30%, about 5% to about 25%, about 5% to about 20%, 10% to about 55%, about 10% to about 50%, about 10% to about 45%, about 10% to about 40%, about 10% to about 35%, about 10% to about 30%, about 10% to about 25%, about 10% to about 20%, 15% to about 55%, about 15% to about 50%, about 15% to about 45%, about 15% to about 40%, about 15% to about 35%, about 15% to about 30%, about 15% to about 25%, or about 15% to about 20% by weight, relative to the total weight of the hair color toning composition.

In certain embodiments, the composition comprises, consists essentially of, or consists of non-aqueous solvents, for example, glycerin, $C_1$-4 alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In some cases, the water-soluble solvent may be selected from the group consisting of one or more glycols, $C_{1-4}$ alcohols, glycerin, or mixtures thereof. In some cases, the water-soluble solvent is selected from the group consisting of hexylene glycol, proplene glycol, caprylyl glycol, glycerin, isopropyl alcohol, or mixtures thereof.

Polyhydric alcohols are also useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, or mixtures thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, or mixtures thereof.

The total amount of the non-aqueous solvents may vary, but in some cases ranges from about 0.01% to about 50% by weight, relative to the total weight of the composition. For example, the total amount of non-aqueous solvents may range from about 1% to about 50%, about 2% to about 50%, about 3% to 50%, about 4% to about 50%, about 5% to about 50%, 1% to about 40%, about 2% to about 40%, about 3% to 40%, about 4% to about 40%, about 5% to about 40%, about 1% to about 35%, about 2% to about 35%, about 3% to 35%, about 4% to about 35%, or about 5% to about 35% by weight, relative to the total weight of the composition. In certain embodiments, the total amount of non-aqueous solvents may range from about 1% to about 10%, about 2% to about 8%, about 3% to about 7%, about 25% to about 45%, about 25% to about 40%, about 25% to about 35%, or about 30% to about 35% by weight, relative to the total weight of the composition.

Thickening Agents

In some embodiments, the hair color toning composition optionally further comprises at least one thickening agent (also referred to as thickeners or viscosity modifying agents). In other embodiments, the hair color toning composition does not comprise a thickening agent.

Useful classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, or mixtures thereof.

In some cases, the thickening agents may include one or more associative thickening polymers such as anionic associative polymers, amphoteric associative polymers, cationic associative polymers, nonionic associative polymers, or mixtures thereof. A non-limiting example of an amphoteric associative polymer is acrylates/beheneth-25 methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), or mixtures thereof. The associative thickening polymers, for instance, the acrylates copolymer and/or the acrylates crosspolymer-4, may be neutralized in water or an aqueous solution with a neutralizing agent before the polymer is added into a hair color toning composition.

In some embodiments, the thickener is chosen from hydroxyethylcellulose, cetyl hydroxyethylcellulose, or combinations thereof.

The total amount of the one or more thickening agents may vary, but in some cases is about 0.1% to about 15%, about 0.1% to about 10%, about 0.1% to about 8%, about 0.1% to about 6%, about 0.15 to about 5%, about 0.1% to about 4%, about 0.1% to about 3%, about 0.1% to about 2%, about 0.1% to about 1%, about 0.5% to about 10%, about 0.5% to about 8%, about 0.5% to about 5%, about 0.5% to about 2%, about 1% to about 10%, about 1% to about 8%, about 1% to about 6%, or about 1% to about 5% by weight, relative to the total weight of the composition.

pH Adjusters

The hair color toning compositions according to the disclosure have a pH ranging from about 7 to about 10.4, such as from about 7.5 to about 10.4, about 8 to about 10.4, about 8.5 to about 10.4, about 9 to about 10.4, or about 9 to about 10. For example, the hair color toning compositions may have a pH of about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, 10.0, about 10.1, about 10.2, about 10.3, or about 10.4. The compositions may therefore, optionally contain acid and/or alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

Additional Components

The composition according to the disclosure may optionally comprise any auxiliary or additional component suitable for use in cosmetic compositions, and in particular suitable for hair color toning compositions. Such components may include, but are not limited to, dyes/pigments in addition to those listed above, silicone compounds, rheology modifying agents such as acrylic polymers, cationic, nonionic, amphoteric or zwitterionic surfactants or mixtures thereof, anionic, cationic, nonionic, amphoteric or zwitterionic polymers or mixtures, film forming agents or polymers, humectants and moisturizing agents, fatty substances other than the described fatty substances, emulsifying agents other than fatty substances, fillers, structuring agents, propellants, shine agents, antioxidants or reducing agents, penetrants, sequestrants, fragrances, buffers, dispersants, conditioning agents (e.g. plant extracts), for instance volatile or non-volatile, modified or unmodified silicones, ceramides, preserving agents, opacifiers, sunscreen agents, and antistatic agents.

II. Methods

It has been discovered that compositions according to the disclosure surprisingly impart improved properties to the hair, such as improved strength, shine, conditioning, feel, detangling, and/or combability, while also imparting excellent color and/or tone to the hair. Therefore, another aspect of the invention pertains to methods of using any of the compositions described herein by applying the compositions to the hair.

In one embodiment, the method comprises applying the hair color toning compositions directly to hair. In further embodiments, the methods comprises mixing the hair color toning compositions with an oxidizing composition (also known as a developer composition) comprising one or more oxidizing agents to form a mixture, and applying the mixture to the hair.

In embodiments comprising oxidizing agents, the at least one oxidizing agent may be chosen, for example, from peroxides, persulfates, perborates, percarbonates, alkali metal bromates, ferricyanides, peroxygenated salts, alkali metal carbonates, or mixtures thereof. Oxidizing agents that may also be used include at least one redox enzyme such as laccases, peroxidases, and 2-electron oxidoreductases, such as uricase, where appropriate in the presence of their respective donor or co-factor.

Oxygen in the air may also be employed as an oxidizing agent.

In some embodiments, the oxidizing agent can be hydrogen peroxide present in an aqueous solution whose titer may range from 1 to 40 volumes, such as from 5 to 40 volumes, from 5 to 30 volumes, or from 5 to 20 volumes.

In another embodiment, the oxidizing agent can be a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. In certain embodiments, the oxidizing agent is hydrogen peroxide.

In general, the oxidizing agent will be present in an amount ranging from about 0.05 to about 50% by weight, such as from about 0.1% to about 30% by weight, from about 0.1% to about 20% by weight, or from about 1% to about 10% by weight, based on the total weight of the developer composition or solution or system in which it is present.

In some embodiments, the developer composition is aqueous or is in the form of an emulsion. The developer composition can contain at least one solvent, chosen from water, organic solvents, and mixtures thereof.

In alternative embodiments, the developer composition is substantially anhydrous. The term "substantially anhydrous" means that the developer composition is either completely free of water or contains no appreciable amount of water, for example, no more than 5% by weight, or no more than 2% by weight, or no more than 1% by weight, based on the weight of the developer composition. It should be noted that this refers for example to bound water, such as the water of crystallization of the salts or traces of water absorbed by the raw materials used in the preparation of the compositions according to embodiments of the disclosure.

When the developer composition is substantially anhydrous, the developer composition may comprise at least one solvent chosen from organic solvents. Suitable organic solvents for use in the developer composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, or mixtures thereof.

The organic solvents for use in the developer composition can include volatile or non-volatile compounds. The organic solvent may, for example, be present in an amount ranging from about 0.5% to about 70% by weight, such as from about 2% to about 60% by weight, preferably from about 5 to about 50% by weight, relative to the total weight of the developer composition or system in which it is present.

The developer composition may be in the form of a powder, gel, liquid, foam, lotion, cream, mousse, and emulsion.

The pH of the developer composition can range from about 2 to about 12, such as from about 6 to about 11, and it may be adjusted to the desired value using acidifying/alkalizing agents that are well known in the art. In certain embodiments, the pH of the developer composition is below 7.

The pH of the composition resulting from mixing together the hair color toning composition and the developer composition (the mixture) may range from about 6.0 to about 6.8, such as about 6.0 to about 6.7, about 6.0 to about 6.6, about 6.0 to about 6.5, about 6.1 to about 6.7, about 6.1 to about 6.6, about 6.1 to about 6.5, about 6.2 to about 6.7, about 6.2 to about 6.6, about 6.2 to about 6.5, about 6.3 to about 6.7, about 6.3 to about 6.6, about 6.3 to about 6.5, about 6.4 to about 6.7, about 6.4 to about 6.6, or about 6.4 to about 6.5. For example, the pH of the mixture may be about 6.0, about 6.1, about 6.2, about 6.3, about 6.4, about 6.5, about 6.6, about 6.7, or about 6.8.

The hair color toning composition or the mixture may be left on the hair for a period of time sufficient to achieve the desired effect. For example, the hair composition or the mixture may be left on the hair for up to one hour, such as from about 3 minutes to about 45 minutes, from about 5 minutes to about 30 minutes, or from about 10 minutes to about 20 minutes. In further embodiments, the hair color toning composition or the mixture may be left on the hair for a period up to about 30 minutes, such as, for example, from about 1 to about 30 minutes, about 1 to about 10 minutes, or about 1 to about 5 minutes. One skilled in the art will be able to determine an appropriate amount of time to leave the hair color toning composition or the mixture on the hair in order to achieve the desired effect. If desired, the composition may, optionally, be shampooed and/or rinsed off the hair.

III. Kits

Another aspect of the invention pertains to kits which comprise any of the hair color toning compositions described herein for use in exemplary methods according to the disclosure. In some embodiments, the kit comprises a hair color toning composition according to the disclosure in a first compartment or container, and a developer composition as described above in a second compartment or container. The developer composition and the hair color toning composition may then be mixed prior to application onto hair.

According to at least one embodiment, the kits comprising the compositions according to the disclosure and the developer composition are free or substantially free of ammonia.

As used herein, the terms "comprising," "having," and "including" (or "comprise," "have," and "include") are used in their open, non-limiting sense.

The terms "a," "an," and "the" are understood to encompass the plural as well as the singular, and are equivalent to "at least one."

Thus, the term "a mixture thereof" or "a combination thereof" also relates to "mixtures thereof" and "combinations thereof." Throughout the disclosure, the terms "a mixture thereof" and "a combination thereof" is used, following a list of elements as shown in the following example where letters A-F represent the elements: "one or more elements selected from the group consisting of A, B, C, D, E, F, and a mixture thereof." The terms "a mixture thereof" or "a combination thereof" do not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts, for example, the salts of the amino acids, the amino sulfonic acids, and the non-polymeric mono, di, and/or tricarboxylic acids, which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and/or softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat" (and its grammatical variations) as used herein also refers to contacting keratinous substrates such as hair with the compositions of the present disclosure.

A "rinse off" product refers to a composition such as a hair color toning composition that is rinsed and/or washed with water either after or during the application of the composition onto the keratinous substrate, and before drying and/or styling said keratinous substrate. At least a portion, and typically most, of the composition is removed from the keratinous substrate during the rinsing and/or washing.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein, unless expressly stated otherwise, means that there is less than about 5% by weight of a specific material added to a composition, based on the total weight of the compositions. Nonetheless, the compositions may include less than about 3%, less than about 2%, less than about 1%, less than about 0.5%, less than about 0.1%, or none of the specified material.

All ranges and values disclosed herein are inclusive and combinable. For examples, any value or point described herein that falls within a range described herein can serve as a minimum or maximum value to derive a sub-range, etc.

Further, unless expressly stated otherwise or when the context of the disclosure clearly dictates otherwise, the language "the at least one X may be present in an amount ranging from Y % to Z %" is to be understood to mean that the total amount of X's present in the composition ranges from Y % to Z %, inclusive of the endpoints. For example, "the at least one thickener may be present in an amount ranging from about 0.01% to about 10%" means that the total amount of thickeners present ranges from about 0.01% to about 10%, and is inclusive of both 0.01% and 10%.

The term "and/or" should be understood to include both the conjunctive and the disjunctive. For example, "A and/or B" means "A and B" as well as "A or B," and expressly covers instances of either, without reference to the other. For example, a composition that comprises "at least one thickener and/or at least one direct dye" means that the disclosure includes compositions comprising one or more thickeners or one or more direct dyes, as well as compositions comprising one or more thickeners and one or more direct dyes.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The following examples serve to illustrate embodiments of the present disclosure without, however, being limiting in nature. It will be apparent to those skilled in the art that various modifications and variations can be made in the delivery system, composition and methods of the invention without departing from the spirit or scope of the invention. Thus, it is intended that the present disclosure cover the modifications and variations that come within the scope of the appended claims and their equivalents.

EXAMPLES

Implementation of the present disclosure is demonstrated by way of the following non-limiting examples.

Example 1—Hair Toner Formulations

The following hair toner formulations (toning or color deposit) according to the disclosure were prepared.

TABLE 1

|  | 1A | 1B | 1C | 1D |
|---|---|---|---|---|
| TAURINE | 0.500 | 0.500 | 0.500 | 0.500 |
| CITRIC ACID | 0.200 | 0.200 | 0.200 | 0.200 |
| ETHANOLAMINE | 0.200 | 0.350 | 0.350 | 0.350 |
| COCO-BETAINE | 0.750 | 0.750 | 0.750 | 0.750 |
| SODIUM C14-16 OLEFIN SULFONATE | 9.000 | 9.000 | 9.000 | 9.000 |
| PPG-5-CETETH-10 PHOSPHATE AND DECETH-3 | 9.000 | 9.000 | 9.000 | 9.000 |
| COCAMIDE MIPA | 6.500 | 6.500 | 6.500 | 6.500 |
| LAURYL ALCOHOL | 1.725 | 1.725 | 1.725 | 1.725 |
| MYRISTYL ALCOHOL | 0.625 | 0.625 | 0.625 | 0.625 |
| CETYL ALCOHOL | 0.150 | 0.150 | 0.150 | 0.150 |
| OLEYL ALCOHOL | 6.000 | 6.000 | 6.000 | 6.000 |
| PEG/PPG-4/12 DIMETHICONE | 1.500 | 1.500 | 1.500 | 1.500 |
| ALCOHOL DENAT., PROPYLENE GLYCOL, AND PPG-2 BUTYL ETHER | 22.00 | 22.00 | 22.00 | 22.00 |
| EDTA, TETRASODIUM EDTA | 0.081 | 0.081 | 0.081 | 0.081 |
| SODIUM SULFITE AND ERYTHORBIC ACID | 0.900 | 0.900 | 0.900 | 0.900 |

TABLE 1-continued

|  | 1A | 1B | 1C | 1D |
|---|---|---|---|---|
| TOLUENE-2,5-DIAMINE | 0.082 | 0.028 | 0.042 | 0.018 |
| 2,4-DIAMINOPHENOXY-ETHANOL HCL | 0.005 | 0.001 | 0.010 | 0.003 |
| m-AMINOPHENOL | 0.080 | 0.015 | 0.028 | 0.015 |
| 4-AMINO-2-HYDROXYTOLUENE |  | 0.018 | 0.021 | 0.015 |
| HYDROXYBENZOMORPHOLINE, 2-AMINO-3-HYDROXYPYRIDINE |  | 0.043 |  | 0.040 |
| p-AMINOPHENOL AND/OR N,N-BIS(2-HYDROXYETHYL)-p-PHENYLENEDIAMINE SULFATE | 0.007 | 0.038 | 0.014 | 0.035 |
| ONE OR MORE OF THIOGLYCERIN, SALT, PRESERVATIVES, FRAGRANCE, VEGETAL EXTRACT | ≤2.000 | | | |
| WATER | Q.S. | | | |
| pH | 8.7-9.6 | | | |

Example 2—Comparative Hair Toner Formulations

The following comparative hair toner formulations (toning or color deposit) formulations are presented below and contain combinations of oxidative dyes (bases and couplers) and/or certain direct dyes that are different from the combinations in the formulations of Example 1. The formulations of Example 2 were used as the benchmark for the desired color or tone to be deposited on hair by the formulations of Example 1.

TABLE 2

|  | 2A | 2B | 2C | 2D |
|---|---|---|---|---|
| ERYTHORBIC ACID AND SODIUM SULFITE | 1.200 | 0.650 | 0.900 | 1.150 |
| ETHANOLAMINE | 0.200 | 0.200 | 0.200 | 0.200 |
| SODIUM C14-16 OLEFIN SULFONATE | 9.000 | 9.000 | 9.000 | 9.000 |
| COCO-BETAINE | 0.750 | 0.750 | 0.750 | 0.750 |
| COCAMIDE MIPA | 6.500 | 6.500 | 6.500 | 6.500 |
| DECETH-3 AND PPG-5-CETETH-10 PHOSPHATE | 9.000 | 9.000 | 9.000 | 9.000 |
| OLEYL ALCOHOL | 6.000 | 6.000 | 6.000 | 6.000 |
| CETYL ALCOHOL | 0.150 | 0.150 | 0.150 | 0.150 |
| LAURYL ALCOHOL | 1.725 | 1.725 | 1.725 | 1.725 |
| MYRISTYL ALCOHOL | 0.625 | 0.625 | 0.625 | 0.625 |
| PEG/PPG-4/12 DIMETHICONE | 1.500 | 1.500 | 1.500 | 1.500 |
| ISOPROPYL ALCOHOL AND PROPYLENE GLYCOL AND PPG-2 BUTYL ETHER | 22.00 | 22.00 | 22.00 | 22.00 |
| TETRASODIUM EDTA, DISODIUM EDTA, EDTA | 0.082 | 0.082 | 0.082 | 0.082 |
| p-PHENYLENEDIAMINE AND/OR N,N-BIS(2-HYDROXYETHYL)-p-PHENYLENEDIAMINE SULFATE AND/OR p-AMINOPHENOL | 0.072 | 0.025 | 0.014 | 0.043 |
| TOLUENE-2,5-DIAMINE |  | 0.030 | 0.046 |  |
| 2,4-DIAMINOPHENOXYETHANOL HCL |  |  | 0.009 |  |
| 2-AMINO-6-CHLORO-4-NITROPHENOL | 0.001 | 0.002 |  | 0.015 |
| 2-METHYLRESORCINOL |  | 0.030 |  | 0.057 |
| 2-NITRO-5-GLYCERYL METHYLANILINE AND/OR 3-NITRO-P-HYDROXYETHYLAMINOPHENOL | 0.006 | 0.014 |  |  |
| 4-AMINO-2-HYDROXYTOLUENE |  | 0.004 | 0.020 |  |
| 4-CHLORORESORCINOL AND/OR RESORCINOL | 0.047 | 0.015 |  | 0.014 |
| m-AMINOPHENOL | 0.034 | 0.009 | 0.027 |  |
| HC RED NO. 3 | 0.004 | 0.006 | 0.003 |  |
| ONE OR MORE OF THIOGLYCERIN, SALT, PRESERVATIVES, FRAGRANCE, VEGETAL EXTRACT | ≤2.000 | | | |
| WATER | Q.S. | | | |

Example 3—Comparative Hair Toner Formulations

The following comparative hair toner formulations were prepared.

TABLE 3

|  | 3A | 3B | 3C | 3D |
|---|---|---|---|---|
| TAURINE | — | — | — | — |
| CITRIC ACID | 1.150 | 0.570 | 0.400 | 0.280 |
| ETHANOLAMINE | 0.440 | 0.440 | 0.440 | 0.440 |
| ERYTHORBIC ACID AND SODIUM SULFITE | 1.150 | 1.150 | 1.150 | 1.150 |
| SODIUM C14-16 OLEFIN SULFONATE | 9.000 | 9.000 | 9.000 | 9.000 |
| COCO-BETAINE | 0.750 | 0.750 | 0.750 | 0.750 |
| DECETH-3 AND PPG-5-CETETH-10 PHOSPHATE | 9.000 | 9.000 | 9.000 | 9.000 |
| COCAMIDE MIPA | 6.500 | 6.500 | 6.500 | 6.500 |
| OLEYL ALCOHOL | 6.00000 | 6.00000 | 6.00000 | 6.00000 |
| LAURYL ALCOHOL | 1.750 | 1.750 | 1.750 | 1.750 |
| ISOPROPYL ALCOHOL, PROPYLENE GLYCOL, AND PPG-2 BUTYL ETHER | 22.00 | 22.00 | 22.00 | 22.00 |
| PEG/PPG-4/12 DIMETHICONE | 1.50000 | 1.50000 | 1.50000 | 1.50000 |
| p-PHENYLENE-DIAMINE | 0.06000 | 0.06000 | 0.06000 | 0.06000 |
| 4-AMINO-2-HYDROXYTOLUENE | 0.08000 | 0.08000 | 0.08000 | 0.08000 |
| 2,4-DIAMINO-PHENOXYETHANOL HCl | 0.00900 | 0.00900 | 0.00900 | 0.00900 |
| m-AMINOPHENOL | 0.01400 | 0.01400 | 0.01400 | 0.01400 |
| EDTA | 0.05800 | 0.05800 | 0.05800 | 0.05800 |
| ADDITIVES AND/OR MISC INGREDIENTS: ONE OR MORE OF THIOGLYCERIN, SALT, PRESERVATIVES, FRAGRANCE, VEGETAL EXTRACT | </=2.000 | </=2.000 | </=2.000 | </=2.000 |
| WATER | Q.S. | Q.S. | Q.S. | Q.S. |
| pH | 5.71 | 6.77 | 8.00 | 8.90 |

Treatment of hair with oxidative dye mixtures (formulations according to the disclosure in Example 1 combined with a developer composition containing an oxidizing agent) results in better smoothness and feel to the hair as compared to treatment of hair with the dye mixtures comprising the comparative formulations in Example 3 combined with a developer composition.

Example 4—Stability Testing of Hair Toner Formulations

The formulations according to the disclosure were stored at different temperatures over a period of time and stability was evaluated visually, by viscosity of the formulation or the mixture of the formulation and developer containing an oxidizing agent (mix). Viscosity was measured using a Rheomat, using a spindle of M2, frequency of 180 seconds.

As an indication of stability, the pH of the formulations and of the mixes only change slightly over various temperatures (room temperature, 4, 37, and 45° C.) and over a period of 8 weeks (initial, 4 weeks and 8 weeks) from 8.7-9.6 and from 6.2-6.8, respectively. The color, appearance, and homogeneity of the formulation also remain same, and the color and clear appearance of the mix does not change at the indicated test conditions.

Example 5—Evaluation of Strength of Treated Hair

Hair treated with clear formulations 5A or 5B (dyes were not present) was subjected to miniature tensile testing (MTT) in order to evaluate the strength of the hair after treatment. The results of both break stress and break extension demonstrate statistically significant improvement in the strength of hair treated with inventive formulation 5A, compared to hair treated with comparative formulation 5B.

TABLE 4

|  | 5A | 5B |
|---|---|---|
| LAURYL ALCOHOL | 5.000 | 2.500 |
| DECETH-3 | 10.00 | 9.000 |
| COCAMIDE MIPA | 7.200 | 6.500 |
| SODIUM SULFITE | 1.000 | 1.000 |
| m-AMINOPHENOL | 0.01400 | 0.0140 |
| ETHANOLAMINE | 0.20000 | 0.410 |
| SODIUM C14-16 OLEFIN SULFONATE | 10.00 | 9.000 |
| 2,4-DIAMINO-PHENOXYETHANOL HCl | 0.009 | 0.009 |
| ERYTHORBIC ACID | 0.150 | 0.150 |
| OLEYL ALCOHOL | 6.000 | 6.000 |
| ISOPROPYL ALCOHOL | — | 10.000 |
| PPG-5-CETETH-10 PHOSPHATE | 1.000 | 0.900 |
| PEG/PPG-4/12 DIMETHICONE | 1.500 | 1.500 |
| 4-AMINO-2-HYDROXYTOLUENE | 0.0800 | 0.0800 |
| EDTA | 0.0580 | 0.0580 |
| COCO-BETAINE | 3.000 | 2.500 |
| p-PHENYLENE-DIAMINE | 0.060 | 0.060 |
| TAURINE | 1.000 | — |
| CITRIC ACID | 0.200 | — |
| DENATURED ALCOHOL, PPG-2 BUTYL ETHER, PROPYLENE GLYCOL | 22.00 | — |
| WATER | Q.S. | Q.S. |
|  | 9.35 | 10.41 |

TABLE 5

| Formulation | Mean | Standard Deviation | CV(%) | CI(95) | Count |
|---|---|---|---|---|---|
| Break Stress | | | | | |
| 5A | 123.2 | 20.53 | 0.1666 | 6.209 | 42 |
| 5B | 105.9 | 20.08 | 0.1895 | 5.679 | 48 |
| Break Extension % | | | | | |
| 5A | 67.96 | 7.212 | 0.1061 | 2.181 | 42 |
| 5B | 61.08 | 6.566 | 0.1075 | 1.858 | 48 |

The above data demonstrates that the formulations according to the disclosure which contain an amino acid such as taurine and a carboxylic acid such as citric acid provide significantly better strength properties to the hair.

Example 6—Evaluation of Tone/Color Deposit

The tone or color that was deposited on hair swatches treated with oxidative hair dye mixtures containing the formulations of the disclosure was compared visually to the tone or color deposited on hair swatches treated with hair dye mixtures containing the comparative formulations.

| Inventive Formulation | Comparative Formulation | Desired tone or color |
|---|---|---|
| 1A | 2A | Golden brown |
| 1B | 2B | Light warm gold with slight pink/violet tone |
| 1C | 2C | Light silvery pinkish ash |
| 1D | 2D | Light beige natural |

It was found that by employing new combinations of dyes in formulations 1A to 1D and replacing some of the dyes which were present in the comparative formulations, the tone or color deposited on hair by oxidative dye mixtures containing formulations prepared in accordance with the disclosure (1A to 1D) matched the performance or the tone or color deposited by oxidative dye mixtures containing formulations 2A to 2D.

The above examples demonstrate that the formulations according to the disclosure unexpectedly provide improved strength, smoothness, and feel to the hair, while achieving shine on hair, stability, and superior toning and color deposit that matched the color/tone achieved by the benchmarks on hair. The color or tone matching was achieved by the formulations according to the disclosure which utilized a different combination of oxidative dyes and/or couplers.

The invention claimed is:

1. A hair color toning composition comprising:
   (a) at least one amino acid;
   (b) at least one carboxylic acid;
   (c) monoethanolamine, present in an amount ranging from about 0.01% to about 1.3% by weight, relative to the total weight of the composition;
   (d) a surfactant mixture comprising (i) at least one amphoteric surfactant, and (ii) at least one surfactant chosen from anionic surfactants or non-ionic surfactants;
   (e) at least one fatty compound;
   (f) at least one oxidation base chosen from toluene-2,5-diamine, acid salts thereof, or solvates thereof;
   (g) a coupler comprising at least one coupler chosen from:
      (I) 2,4-diaminophenoxyethanol, derivatives thereof, addition salts thereof, solvates thereof, or solvates of salts thereof;
      (II) meta-aminophenol (1-hydroxy-3-aminobenzene), derivatives thereof, addition salts thereof, solvates thereof, or solvates of salts thereof; or
      (III) mixtures thereof; and
   (h) at least one solvent,
   wherein the hair color toning composition has a pH ranging from about 7 to about 10.4.

2. The hair color toning composition according to claim 1, wherein the at least one amino acid is chosen from taurine, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine, or mixtures thereof.

3. The hair color toning composition according to claim 1, wherein the total amount of amino acids ranges from about 0.05% to about 5% by weight, relative to the total weight of the composition.

4. The hair color toning composition according to claim 1, wherein the at least one carboxylic acid is chosen from oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, trimesic acid, propane-1,2,3-tricarboxylic acid, or mixtures thereof.

5. The hair color toning composition according to claim 1, wherein the at least one carboxylic acid comprises citric acid.

6. The hair color toning composition according to claim 1, wherein the total amount of carboxylic acids ranges from about 0.01% to about 3% by weight, relative to the weight of the composition.

7. The hair color toning composition according to claim 1, wherein the at least one fatty compound is chosen from C12-C22 fatty alcohols.

8. The hair color toning composition according to claim 1, wherein the total amount of oxidation base ranges from about 0.001% to about 20% by weight, relative to the total weight of the composition.

9. The hair color toning composition according to claim 1, wherein the total amount of coupler ranges from about 0.001% to about 20% by weight, relative to the total weight of the composition.

10. The hair color toning composition according to claim 1, further comprising:
    (i) one or more additional oxidative bases chosen from p-aminophenol, N, N-bis((2-hydroxyethyl)-p-phenylenediamine sulfate, Hydroxypropyl bis (N-hydroxyethyl-p-phenylenediamine) HCl, O-Aminophenol, N-methyl-p-aminophenol sulfate, N-methyl-p-aminophenol sulfate, 2,3-Diaminohydropyrazolo pyrazolone dimethosulfate, 1-Hydroxyethyl 4,5-diamino pyrazole sulfate, 2-[(3-1-Aminopyrazolo[1,5-A]pyridin-2-yl)oxy]ethanol hydrochloride, derivatives thereof, addition salts thereof, solvates thereof, solvates of salts thereof, or mixtures thereof, and/or
    (ii) one or more additional couplers chosen from hydroxybenzomorpholine (hydroxy-6-benzomorpholine), 2-amino-3-hydroxypyridine, m-aminophenol, 2-methyl-5-hydroxyethylaminophenol, hydroxy-6-indole, 2-amino-3-hydroxypyridine, 5-amino-6-chloro-o-cresol, 1-naphthol, derivatives thereof, addition salts thereof, solvates thereof, solvates of salts thereof, or mixtures thereof.

11. The hair color toning composition according to claim 1, further comprising at least one conditioning agent.

12. The hair color toning composition according to claim 1, wherein the monoethanolamine is present in the composition in an amount ranging from about 0.1% to about 1.3% by weight, relative to the total weight of the composition.

13. The hair color toning composition according to claim 1, wherein the at least one amino acid comprises taurine and the at least one carboxylic acid comprises citric acid.

14. A method for altering the tone or color of the hair, comprising mixing (i) a hair color toning composition with (ii) an oxidizing composition to form a mixture having a pH ranging from about 6.0 to about 6.8, and applying the mixture to the hair, wherein:
  (i) the hair color toning composition comprises:
    (a) at least one amino acid,
    (b) at least one carboxylic acid,
    (c) monoethanolamine, present in an amount ranging from about 0.01% to about 1.3% by weight, relative to the total weight of the composition,
    (d) a surfactant mixture comprising (i) at least one amphoteric surfactant and (ii) at least one surfactant chosen from anionic or non-ionic surfactants,
    (e) at least one fatty compound,
    (f) at least one oxidation base chosen from toluene-2,5-diamine, acid salts thereof, or solvates thereof;
    (g) a coupler system comprising at least one coupler chosen from:
      (I) 2,4-diaminophenoxyethanol, derivatives thereof, addition salts thereof, solvates thereof, or solvates of salts thereof;
      (II) meta-aminophenol (1-hydroxy-3-aminobenzene), derivatives thereof, addition salts thereof, solvates thereof, or solvates of salts thereof; or
      (III) mixtures thereof; and
    (h) at least one solvent;
    wherein the hair color toning composition has a pH ranging from about 7 to about 10.4, and
  (ii) the oxidizing composition comprises at least one oxidizing agent.

15. The method according to claim 14, wherein the at least one amino acid is chosen from taurine, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine, or mixtures thereof.

16. The method according to claim 14, wherein the total amount of amino acid ranges from about 0.05% to about 5% by weight, relative to the weight of the hair color toning composition.

17. The method according to claim 14, wherein the at least one carboxylic acid is chosen from oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, trimesic acid, propane-1,2,3-tricarboxylic acid, or mixtures thereof.

18. The method according to claim 14, wherein the total amount of carboxylic acids ranges from about 0.01% to about 3% by weight, relative to the weight of the hair color toning composition.

19. A hair color toning composition comprising:
  (a) from about 0.1% to about 2% taurine by weight, relative to the weight of the composition,
  (b) from about 0.1% to about 3% citric acid by weight, relative to the weight of the composition,
  (c) from about 0.1% to about 1.3% monoethanolamine by weight, relative to the weight of the composition,
  (d) at least one surfactant,
  (e) at least one fatty compound chosen from C12-C22 fatty alcohols,
  (f) at least one oxidation base chosen from toluene-2,5-diamine, acid salts thereof, or solvates thereof;
  (g) at least one coupler chosen from 2,4-diaminophenoxyethanol HCl, derivatives thereof, addition salts thereof, solvates thereof, or solvates of salts thereof; meta-aminophenol, derivatives thereof, addition salts thereof, solvates thereof, or solvates of salts thereof; or mixtures thereof; and
  (h) at least one solvent,
  wherein the hair color toning composition has a pH ranging from about 8.5 to about 10.

20. The hair color toning composition according to claim 19, wherein the coupler comprises 2,4-diaminophenoxyethanol HCl and meta-aminophenol.

* * * * *